(12) United States Patent
Rohl et al.

(10) Patent No.: US 10,617,281 B2
(45) Date of Patent: *Apr. 14, 2020

(54) BALLOON CATHETER SUTURING SYSTEMS, METHODS, AND DEVICES HAVING PLEDGETS

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: James P. Rohl, Prescott, WI (US); David R. Wulfman, Minneapolis, MN (US); Brian T. Berg, St. Paul, MN (US); Joseph Thomas Delaney, Jr., Minneapolis, MN (US); Brian J. Tischler, Shoreview, MN (US); Peter M. Pollak, Atlantic Beach, FL (US); Harold M. Burkhart, Oklahoma City, OK (US); Joseph A. Dearani, Rochester, MN (US); Sorin V. Pislaru, Rochester, MN (US)

(73) Assignees: BOSTON SCIENTIFIC SCIMED, INC, Maple Grove, MN (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/236,274

(22) Filed: Dec. 28, 2018

(65) Prior Publication Data
US 2019/0174994 A1    Jun. 13, 2019

Related U.S. Application Data

(63) Continuation of application No. 15/003,924, filed on Jan. 22, 2016, now Pat. No. 10,285,569.
(Continued)

(51) Int. Cl.
*A61B 1/00* (2006.01)
*A61B 17/04* (2006.01)
(Continued)

(52) U.S. Cl.
CPC ...... *A61B 1/00082* (2013.01); *A61B 1/00087* (2013.01); *A61B 1/00147* (2013.01);
(Continued)

(58) Field of Classification Search
CPC ............ A61B 1/00082; A61B 1/00087; A61B 17/0644; A61B 1/3137; A61B 17/0469;
(Continued)

(56) References Cited

U.S. PATENT DOCUMENTS 4,784,133 A    11/1988  Mackin
4,961,738 A *  10/1990  Mackin .............. A61B 1/00082
                                                    600/116
(Continued)

FOREIGN PATENT DOCUMENTS

CA    2495562 A1    2/2004
CN    102186509 A2    9/2011
(Continued)

*Primary Examiner* — Amy R Weisberg
(74) *Attorney, Agent, or Firm* — Seager, Tufte & Wickhem, LLP

(57) ABSTRACT

A direct visualization catheter includes an elongate shaft defining a lumen and having a distal end portion and a proximal end portion and a transparent balloon attached to the distal end portion of the shaft. The balloon includes a first layer comprising a thermoset polymer and a plurality of
(Continued)

polymeric fibers at least partially embedded in the thermoset polymer and a second layer disposed on the first layer and comprising a hydrogel.

19 Claims, 28 Drawing Sheets

Related U.S. Application Data

(60) Provisional application No. 62/106,936, filed on Jan. 23, 2015, provisional application No. 62/107,068, filed on Jan. 23, 2015.

(51) Int. Cl.

| | | |
|---|---|---|
| *A61B 17/064* | (2006.01) | |
| *A61M 25/10* | (2013.01) | |
| *A61B 1/018* | (2006.01) | |
| *A61B 1/05* | (2006.01) | |
| *A61B 1/313* | (2006.01) | |
| *A61B 17/122* | (2006.01) | |
| *A61B 1/06* | (2006.01) | |
| *A61B 8/12* | (2006.01) | |
| *A61B 17/00* | (2006.01) | |
| *A61B 90/30* | (2016.01) | |
| *A61B 90/00* | (2016.01) | |
| *A61B 17/068* | (2006.01) | |
| *A61B 17/06* | (2006.01) | |
| *A61B 17/128* | (2006.01) | |

(52) U.S. Cl.
CPC ............... *A61B 1/018* (2013.01); *A61B 1/05* (2013.01); *A61B 1/0676* (2013.01); *A61B 1/3137* (2013.01); *A61B 8/12* (2013.01); *A61B 17/0401* (2013.01); *A61B 17/0469* (2013.01); *A61B 17/0644* (2013.01); *A61B 17/122* (2013.01); *A61M 25/1029* (2013.01); *A61B 17/068* (2013.01); *A61B 17/1227* (2013.01); *A61B 17/1285* (2013.01); *A61B 2017/00526* (2013.01); *A61B 2017/00783* (2013.01); *A61B 2017/00902* (2013.01); *A61B 2017/00907* (2013.01); *A61B 2017/0406* (2013.01); *A61B 2017/048* (2013.01); *A61B 2017/0409* (2013.01); *A61B 2017/0472* (2013.01); *A61B 2017/06042* (2013.01); *A61B 2017/0649* (2013.01); *A61B 2090/306* (2016.02); *A61B 2090/309* (2016.02); *A61B 2090/3612* (2016.02); *A61F 2220/0008* (2013.01); *A61F 2220/0016* (2013.01); *A61M 25/1002* (2013.01); *A61M 2025/105* (2013.01); *A61M 2025/1075* (2013.01); *A61M 2025/1088* (2013.01)

(58) Field of Classification Search
CPC ....... A61B 1/05; A61B 1/0676; A61B 1/0047; A61B 1/018; A61B 8/12; A61B 17/122; A61B 17/0401; A61B 2090/306; A61B 17/068; A61B 17/1227; A61B 2017/00902; A61B 2017/06042; A61B 2017/0649; A61B 17/1285; A61B 2017/048; A61B 2017/00786; A61B 2090/309; A61B 2017/0409; A61B 2090/3612; A61B 2017/0406; A61B 2017/00526; A61B 2017/0472; A61B 2017/00907; A61B 17/12136; A61B 2017/22051; A61B 2017/22065; A61B 2017/3486; A61B 17/0466; A61B 17/0482; A61B 17/0406; A61M 25/1029; A61M 2025/1075; A61M 25/1002; A61M 2025/1088; A61M 2025/105; A61M 2025/1052; A61M 2025/1065; A61M 2025/107; A61F 2220/0016; A61F 2220/0008

See application file for complete search history.

(56) References Cited

U.S. PATENT DOCUMENTS

| | | | |
|---|---|---|---|
| 5,254,089 A | 10/1993 | Wang | |
| 5,330,490 A * | 7/1994 | Wilk | ................. A61B 1/00082 |
| | | | 606/153 |
| 5,509,899 A * | 4/1996 | Fan | ....................... A61L 29/06 |
| | | | 604/103.14 |
| 5,588,951 A | 12/1996 | Zhu et al. | |
| 5,709,653 A | 1/1998 | Leone | |
| 5,762,604 A | 6/1998 | Kieturakis | |
| 5,833,682 A | 11/1998 | Amplatz et al. | |
| 5,876,426 A | 3/1999 | Kume et al. | |
| 5,964,751 A | 10/1999 | Amplatz et al. | |
| 6,161,543 A | 12/2000 | Cox et al. | |
| 6,517,533 B1 | 2/2003 | Swaminathan | |
| 6,986,775 B2 | 1/2006 | Morales et al. | |
| 8,409,224 B2 | 4/2013 | Shriver | |
| 8,858,573 B2 | 10/2014 | Fortson et al. | |
| 8,864,778 B2 | 10/2014 | Fortson et al. | |
| 2002/0055757 A1 | 5/2002 | Torre et al. | |
| 2002/0068180 A1* | 6/2002 | Yang | ..................... A61L 29/085 |
| | | | 428/447 |
| 2003/0120264 A1 | 6/2003 | Lattouf | |
| 2003/0158517 A1 | 8/2003 | Kokish | |
| 2004/0101644 A1 | 5/2004 | Kinoshita et al. | |
| 2004/0127932 A1* | 7/2004 | Shah | ........................ A61F 6/04 |
| | | | 606/193 |
| 2005/0080313 A1 | 4/2005 | Stewart et al. | |
| 2005/0096673 A1 | 5/2005 | Stack et al. | |
| 2005/0119523 A1* | 6/2005 | Starksen | .......... A61B 17/00234 |
| | | | 600/109 |
| 2005/0197530 A1 | 9/2005 | Wallace et al. | |
| 2005/0245882 A1 | 11/2005 | Elkins et al. | |
| 2005/0261721 A1 | 11/2005 | Radisch et al. | |
| 2006/0142784 A1* | 6/2006 | Kontos | ............ A61B 17/00234 |
| | | | 606/139 |
| 2007/0129735 A1 | 6/2007 | Filipi et al. | |
| 2007/0233170 A1* | 10/2007 | Gertner | .............. A61B 17/0401 |
| | | | 606/192 |
| 2007/0287886 A1* | 12/2007 | Saadat | .................. A61B 1/0008 |
| | | | 600/115 |
| 2007/0293724 A1 | 12/2007 | Saadat et al. | |
| 2008/0188766 A1* | 8/2008 | Gertner | .............. A61B 17/0401 |
| | | | 600/561 |
| 2008/0275473 A1 | 11/2008 | Filipi et al. | |
| 2009/0082634 A1 | 3/2009 | Kathrani et al. | |
| 2009/0143640 A1 | 6/2009 | Saadat et al. | |
| 2009/0198216 A1 | 8/2009 | Muni et al. | |
| 2010/0010311 A1 | 1/2010 | Miller et al. | |
| 2010/0174235 A1* | 7/2010 | Yamaguchi | ........... A61L 29/085 |
| | | | 604/103.08 |
| 2011/0009895 A1* | 1/2011 | Gertner | .............. A61B 17/0401 |
| | | | 606/191 |
| 2011/0213400 A1* | 9/2011 | Ahmann | ............ A61B 17/7097 |
| | | | 606/191 |
| 2012/0016383 A1 | 1/2012 | Sauer et al. | |
| 2012/0065674 A1* | 3/2012 | Levy | .................... A61B 17/0057 |
| | | | 606/214 |
| 2012/0065729 A1 | 3/2012 | Pintor et al. | |
| 2012/0071901 A1* | 3/2012 | Heneveld | ........... A61B 17/0469 |
| | | | 606/145 |
| 2013/0226131 A1* | 8/2013 | Bacino | .................. A61L 29/146 |
| | | | 604/500 |
| 2013/0253641 A1 | 9/2013 | Lattouf | |
| 2014/0249563 A1 | 9/2014 | Malhi et al. | |
| 2015/0094740 A1* | 4/2015 | Gagne | .............. A61B 17/00008 |
| | | | 606/144 |

(56) References Cited

U.S. PATENT DOCUMENTS

| | | |
|---|---|---|
| 2015/0314110 A1 | 11/2015 | Park |
| 2015/0327754 A1 | 11/2015 | Leefang et al. |
| 2016/0045098 A1 | 2/2016 | Tsubouchi |
| 2016/0213237 A1* | 7/2016 | Rohl .................... A61B 17/122 |
| 2017/0079717 A1* | 3/2017 | Walsh .................... A61B 18/24 |
| 2017/0189006 A1 | 7/2017 | Shluzas et al. |

FOREIGN PATENT DOCUMENTS

| | | |
|---|---|---|
| CN | 102813994 A | 12/2012 |
| CN | 103228317 A | 7/2013 |
| EP | 2005081202 A1 | 9/2005 |
| EP | 1870018 A2 | 12/2007 |
| EP | 2508222 A1 | 10/2012 |
| JP | 04-246367 A | 9/1992 |
| JP | 106507809 A | 9/1994 |
| JP | 09-507148 A | 7/1997 |
| JP | H1051589 A | 2/1998 |
| JP | H10506304 A | 6/1998 |
| JP | 2003-225240 A | 8/2003 |
| JP | 2004-065413 A | 3/2004 |
| JP | 2004-511264 A | 4/2004 |
| JP | 2006-504463 A | 2/2006 |
| JP | 2007535970 A | 12/2007 |
| JP | 2009-543667 A | 12/2009 |
| JP | 2012-192196 A | 10/2012 |
| JP | 2014-528768 A | 10/2014 |
| WO | 9221292 A2 | 12/1992 |
| WO | 9518647 A2 | 7/1995 |
| WO | 9609086 A1 | 3/1996 |
| WO | 0172238 A2 | 10/2001 |
| WO | 2004039445 A1 | 5/2004 |
| WO | 2005037363 A2 | 4/2005 |
| WO | 2005081202 A1 | 9/2005 |
| WO | 2007147060 A2 | 12/2007 |
| WO | 2008011261 A2 | 1/2008 |
| WO | 2012034712 A1 | 3/2012 |
| WO | 2013024466 A2 | 2/2013 |
| WO | 2013159066 A1 | 10/2013 |

* cited by examiner

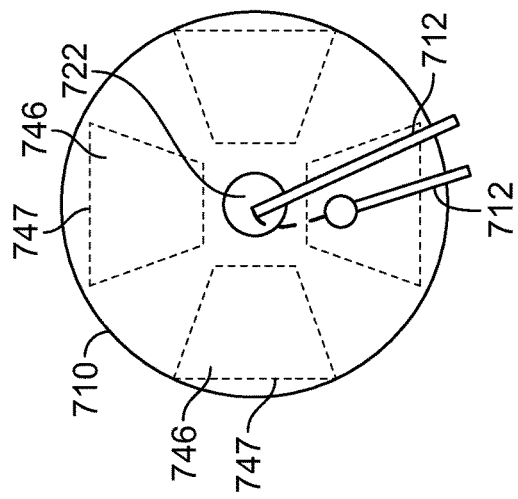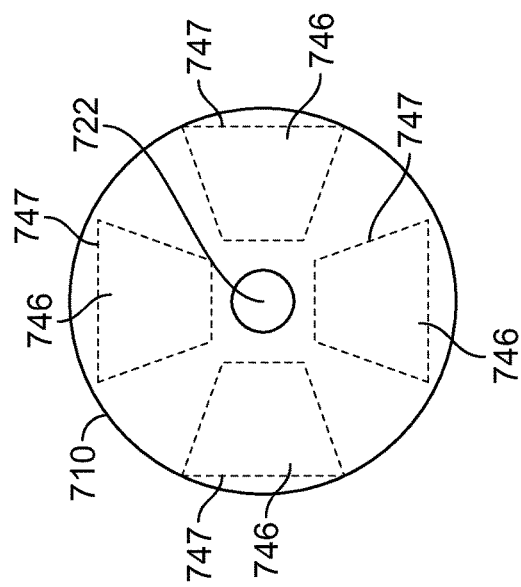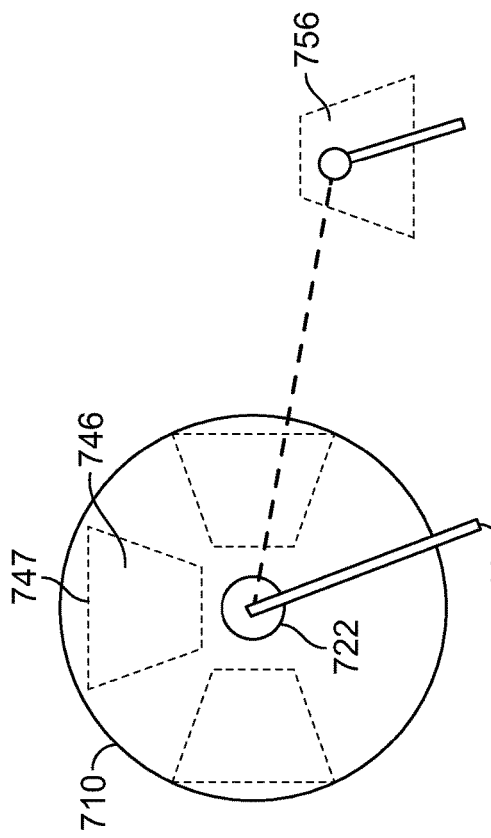

BALLOON CATHETER SUTURING SYSTEMS, METHODS, AND DEVICES HAVING PLEDGETS

PRIORITY CLAIM OF PRIORITY

This application is a continuation of U.S. application Ser. No. 15/003,924, filed Jan. 22, 2016; which claims the benefit of priority under 35 U.S.C. § 119 to U.S. Provisional Application Ser. No. 62/106,936, filed on Jan. 23, 2015, and U.S. Provisional Application Ser. No. 62/107,068 filed Jan. 23, 2015, the entire contents of which are hereby incorporated by reference.

TECHNICAL FIELD

This invention relates to balloon catheters suturing systems, methods, and devices. For example, balloon catheter suturing systems, methods, and devices provided herein can include pledgets.

BACKGROUND

Heart function can be significantly impaired when a heart valve is not performing properly. Potential causes for heart valve malfunction include dilation of an annulus around the valve, ventricular dilation, and a prolapsed or misshapen valve leaflet. When the heart valve is unable to close properly, blood within a heart chamber can leak backwards, through the valve, which is commonly referred to as regurgitation. Valve regurgitation may be treated by replacing or repairing a diseased valve. The most common method of correcting tricuspid valve regurgitation is to reduce the annulus by bringing the anterior and septal leaflets closer together using sutures. In some cases, precut sheet pieces of polytetra-fluorethylene (PTFE), also known as pledgets, are used with the sutures to cushion the load of the suture against host tissue.

Although open heart surgery is one method for treating the diseased valve, a less invasive methods of treatment would be more desirable for many patients. Minimally invasive procedures, however, are significantly limited by the lack of adequate visualization through blood within a patient's beating heart. Accordingly, there is a need for alternative devices and methods for treating heart valve disease that provides adequate visualization and suture delivery for users during a minimally invasive procedure.

SUMMARY

Balloon catheter suturing systems provided herein can be used to suture one or more anatomical locations using less invasive techniques while providing visualization of the anatomical location.

In some aspects, balloon catheter suturing systems provided herein include an elongate shaft defining a lumen and having a distal end portion and a proximal end portion, a balloon attached to the distal end portion, and at least a first pledget secured to the balloon by a portion of the balloon catheter suturing system adjacent the balloon. In some cases, the balloon catheter suturing system includes at least one fastener adapted to fasten the first pledget to an anatomic structure when the balloon catheter suturing system is positioned within a patient.

In some cases, the first pledget is part of the transparent wall. In some cases, the first pledget is held by an internal pledget support structure within the transparent wall of the balloon. In some cases, the first pledget is held by a first pledget support structure outside the transparent wall of the balloon distal to the balloon.

In some cases, balloon catheter suturing systems further comprise a second pledget held by a second pledget support structure proximal to the first pledget, wherein at least one fastener is adapted to fasten the first and second pledgets together on opposite sides of the anatomic structure. In some cases, the second pledget is positioned within the transparent wall of the balloon. In some cases, the second pledget is positioned outside of the transparent wall.

In some cases, the first pledget is defined by weakened sections defining one or more tear lines around the first pledget in the transparent wall. In some cases, the first pledget is adapted to delaminate from a portion of the transparent wall. In some cases, the transparent wall comprises at least a first layer comprising a thermoset polymer and a plurality of polymeric fibers at least partially embedded in the thermoset polymer. In some cases, the transparent wall comprises at least a second layer disposed on the first layer, wherein the second layer comprises a hydrogel.

In some cases, the balloon catheter suturing system can include a transparent wall including at least a first layer comprising a thermoset polymer and a plurality of polymeric fibers at least partially embedded in the thermoset polymer. In some cases, the transparent wall can include at least a second layer disposed on the first layer. In some cases, the second layer can include a hydrogel. In some cases, the polymeric fibers can be electrospun fibers randomly oriented within the thermoset polymer. In some cases, the thermoset polymer comprise a silicone, such as polydimethylsiloxane (PDMS).

The balloon catheter suturing system can have any suitable balloon shape. In some cases, the balloon can be configured such that sutures are passed through the balloon. In some cases, the balloon can define a working channel there through. In some cases, the balloon is a weeping balloon.

In some aspects, a method for repairing a heart valve in a patent can include advancing a balloon end of a balloon catheter into an atrium of a heart, imaging a portion of a heart valve, passing a suture through at least one detachable section to suture a portion of the heart valve to the at least one detachable section, and separating the at least one detachable section from the balloon catheter. The balloon catheter can include one or more elongate shafts in fluid communication with a balloon having a transparent wall. In some cases, the transparent wall can define the at least one detachable section. In some cases, the transparent wall can define multiple detachable sections. In some cases, a portion of a heart valve is imaged through the transparent wall using an imaging element disposed within the balloon through the one or more elongate shafts. In some cases, the at least one detachable section is separated from the balloon catheter by deflating the balloon and removing the balloon catheter from the heart. In some cases, the transparent wall defines the one or more detachable sections with weakened tear lines that tear when the balloon is removed from the heart. In some cases, a plurality of sutures are attached to multiple parts of a heart valve through a plurality of detachable sections prior to separating the plurality of detachable sections. In some cases, the heart valve is a tricuspid valve. In some cases, a valve annulus is sutured to the at least one detachable section.

The details of one or more embodiments of direct visualization devices, systems, and methods provided herein are set forth in the accompanying drawings and the description below. Other features, objects, and advantages will be apparent from the description and drawings, and from the claims.

DESCRIPTION OF DRAWINGS

FIG. 3A depicts a distal end of the system. FIGS. 3B and 3C depict a controlling handle for the system. FIGS. 3D-3I depict the system being used to suture the valve annulus of a tricuspid valve. FIG. 3I depicts the pledgets and suturing thread in isolation.

FIGS. 7A-7C and 8A-8C depict how another exemplary balloon catheter suturing system provided herein can be used to suture tissue and leave pledgets.

DETAILED DESCRIPTION

Balloon catheter suture devices, systems and methods provided herein include features that improve minimally invasive surgical techniques used during a heart valve repair procedure such as, but not limited to, procedures that suture one or more heart valve leaflets. Exemplary procedures include those that bicuspidizes a tricuspid valve, edge to edge stitching techniques (or Alfieri stitches), mitral valve stitches, closures of paravalvular leaks, percutaneous paravalvular leak closure, and/or percutaneous closure of pre-valvular leaks. The term "suture" is used herein to refer to any fastening of anatomical structures, which can be made with any suitable fastener including suturing thread, clips, staples, hooks, tacks, clamps, etc.

Balloon catheter suture devices, systems, and methods provided herein include pledgets retained at an external end of the balloon catheter suturing device. The pledgets are adapted to be sutured to an anatomical location, separate from the balloon catheter, and remain with a resulting suture. As used herein, the term "pledget" will refer to a piece of material that is intended be sutured to an anatomical location. In some cases, the wall of the balloon can include portions arranged to be sutured to an anatomical location through the transparent wall and to separate from the remainder of the balloon catheter to become a pledget. In some cases, balloon catheter suturing devices, systems, and methods provided herein can include one or more pledgets held by the balloon catheter suturing devices and systems provided herein and positioned inside and/or outside the balloon such that the pledget(s) can be secured to an anatomical location using one or more fasteners. In some cases, balloon catheter suturing devices, systems, and methods provided herein can include cooperating pledgets that are arranged to clamp around an anatomical structure have one or more fasteners passed there through.

Balloon catheter suture devices, systems, and methods provided herein can allow for direct visualization of a target location, which can provide anatomy and pathology identification as well as device placement visual feedback to the physician user during a minimally invasive method. Balloon catheter suturing devices, systems, and methods provided herein can include an elongate, compliant balloon having a transparent wall. In some cases, the transparent wall can include portions arranged to be sutured to an anatomical location through the transparent wall and to separate from the remainder of the balloon catheter. In some case, the balloon can include pores to allow for the balloon to "weep" to provide a visually clear area surrounding the balloon. In some cases, the balloon wall (e.g., a transparent balloon wall) can have a structure that limits the propagation of tears. In some cases, as discussed below, the balloon all can include polymeric fibers within a matrix of a second material.

Figure 1A:
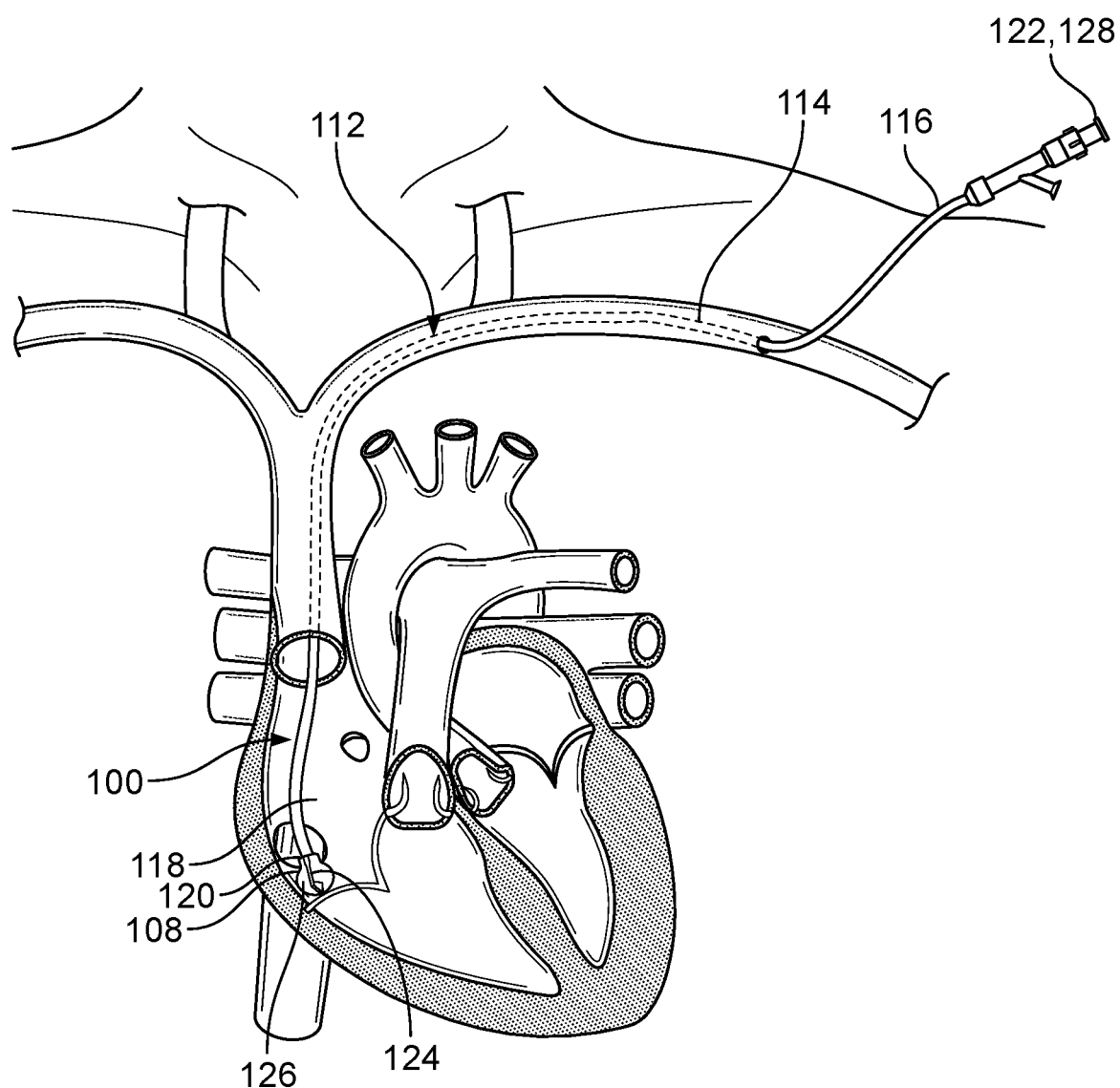
FIG. 1A is an illustration of an exemplary balloon catheter suturing system within a human anatomy.

FIG. 1A shows an exemplary balloon catheter suturing system 100 within a human anatomy. Balloon catheter visualization system 100 can be inserted into a right atrium of a heart through a brachial vein or a jugular vein. As shown in FIG. 1A, balloon catheter suturing system 100 includes an elongate shaft or tubular body 112 having a proximal end portion 114 with a proximal end 116 and a distal end portion 118 with a distal end 120. Proximal end portion 114 can couple to a manifold 122. Distal end portion 118 can include an integrated camera (not shown), a fastening tool 124 with a fastener and at least one balloon 108 (also described as balloon member). Integrated camera and fastening tool 124 can be disposed within balloon 108. As shown in FIG. 1A, balloon 108 can form a distal tip of balloon catheter suturing system 100. The fastening tool 124 can pass a fastener through the balloon to suture an anatomical location outside the balloon. The balloon can be filled with an inflation medium, such as saline solution, that can be safely delivered to the patient, thus leakage from resulting holes in the balloon caused by the passing of the fastener through the balloon can be tolerated.

Balloon catheter suturing system 100 can include a pledget 126 located distal to fastening tool 124 such that a fastener delivered through the balloon is also delivered through pledget 126 to suture pledget 126 to an anatomical location. Pledget 126 can, in some cases, be a part of the balloon wall of balloon 108 adapted to tear away from the balloon wall. In some cases, pledget 126 is laminated to an outside surface of the balloon wall. In some cases, a balloon wall can include weakened sections or weakened tear lines such that pledget 126 tears away from balloon 108 to leave a pledget sized hole. In some cases, pledget 126 can be held within balloon 108. In some cases, pledget 126 can be held adjacent the exterior of balloon 108. These different options are explained in further detail below.

In FIG. 1A, balloon catheter suturing system 100 includes at least one tubular body 112 defining a lumen (not shown). In some cases, balloon catheter suturing system 100 can include multiple tubular bodies, in which each tubular body defines at least one lumen. Each tubular body 112 can optionally include multiple lumens, for example, coaxial or non-coaxial lumens. Balloon catheter suturing system 100 can have one or more lumens that extend partially or fully thorough one or more tubular bodies 112. One or more lumens can be used as a conduit adapted to receive components, e.g., integrated camera or fastener tools, and/or inflation media, e.g., saline. In some cases, one or more lumens can be adapted to jet inflation media, e.g., saline, into distal end portion 118 of balloon catheter suturing system 100.

Manifold 122 generally connects an external fluid supply to one or more lumens of balloon catheter suturing system 100. Manifold 122 can include one or more ports 128 to facilitate a fluid connection to another medical device or a fluid source. For example, port 128 can supply saline solution into one or more lumens of tubular body 112. Manifold 122 may be coupled to tubular body 112 directly or indirectly. In some cases, a flexible tubing, sometimes referred to as a strain relief tubing, is coupled between manifold 122 and the tubular body 112 at the proximal end 116 to provide a longitudinal tapered transition between manifold 122 and tubular body 112. Flexible tubing can help to increase kink resistance of tubular body 112 at proximal end portion 114.

Figure 1B:
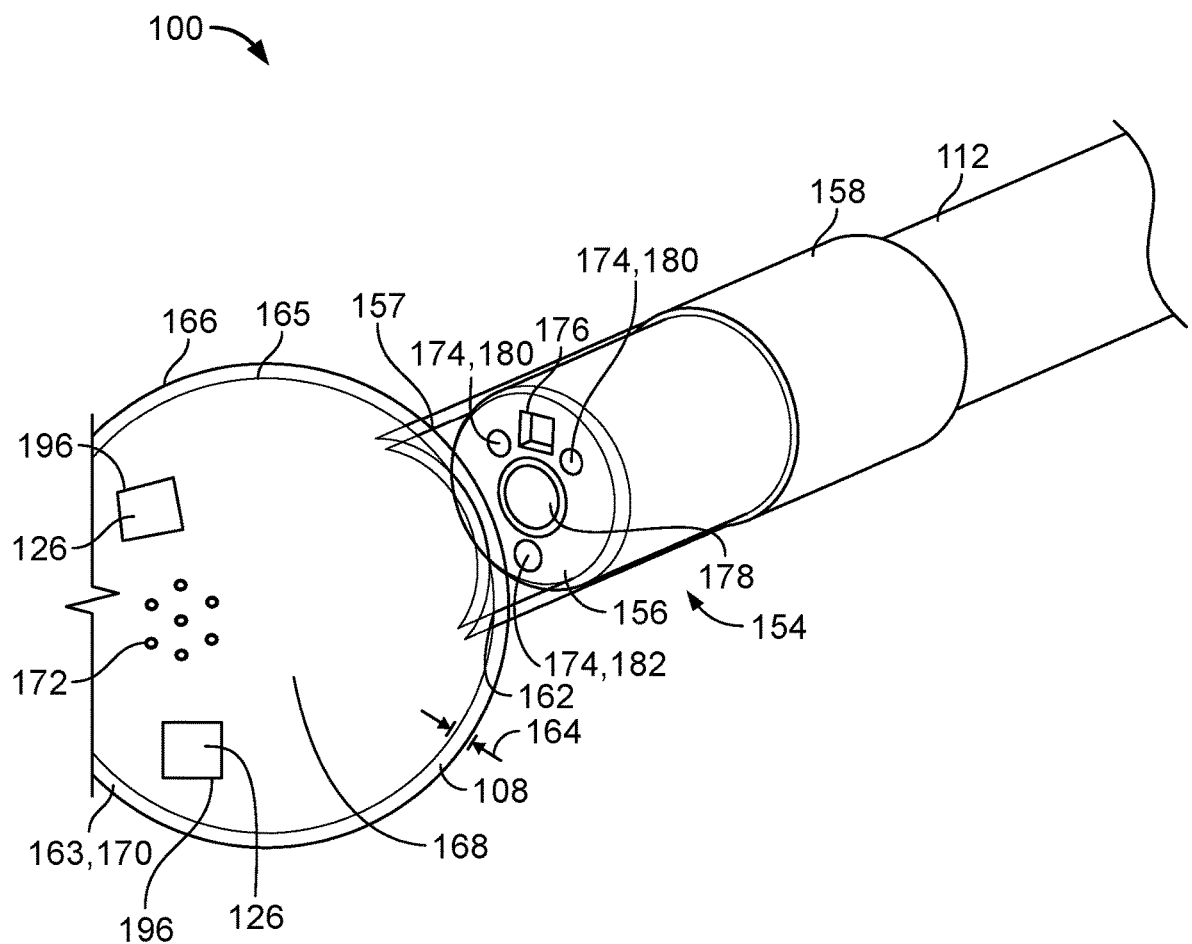
FIG. 1B is a perspective view of a distal end portion of an exemplary balloon catheter having detachable pledgets.

FIG. 1B depicts an distal end of exemplary balloon catheter system 100 having a balloon 108 having tear lines 196, or weakened sections, in the balloon wall 164 that define pledgets 126. Pledgets 126 are adapted to be sutured to anatomical locations and separated from balloon 108. As shown in FIG. 1B, balloon catheter suturing system 100 that includes an elongate, tubular body 112 with a distal end portion 154. In FIG. 1B, a distal end 156 of distal end portion 154 can be either directly or indirectly coupled to a balloon 108. For example, tubular body 112 can be coupled to balloon 108 indirectly by using an intermediate catheter shaft 157. As shown in FIG. 1B, intermediate catheter shaft 157 couples to a proximal end 162 of balloon 108 and a catheter interface portion 158 of tubular body 112.

In FIG. 1B, balloon 108 is disposed proximate to distal end 156 of tubular body 112. Balloon 108 can include the proximal end 162, a distal end 163 and a wall 164 that extends from an interior surface 165 to an exterior surface 166. As shown in FIG. 1B, balloon 108 forms a distal tip 170 of balloon catheter suturing system 100. As discussed herein, balloon 108 can be filled with an inflation media in an interior cavity 168 defined between proximal and distal ends 162, 163. Also discussed herein, balloon 108 can include a weeping balloon structure, i.e., a balloon structure that defines one or more perforations 172 extending through wall 164.

As shown in FIG. 1B, distal end of tubular body can include a plurality of lumens 174. Each lumen of plurality of lumens 174 can longitudinally extend through tubular body 112 entirely or partially there through. Each lumen can be formed from one of various cross-sectional shapes, e.g., circle, oval, slot, square, rectangular, triangular, trapezoid, rhomboid, or irregular shape. The shape of the lumen may facilitate receiving other components of balloon catheter suturing system 100. For example, as discussed herein, one or more lumens 174 can be used to receive a fastening tool (not shown), a camera 176, fiber optic light cables (not shown), electrical cables (not shown), inflation media and combinations thereof. In FIG. 1B, tubular body can define a central lumen 178 for receiving a fastening tool (not shown) for delivering a fastener (not shown), two lumens for receiving fiber optic light cables 180, one lumen for delivering inflation media 182, and one lumen for receiving camera 176.

Pledgets 126 can be sutured to an anatomical location and separated from balloon 108 after suturing to become pledgets. In some cases, pledgets 126 are laminated onto the wall of balloon 108 such that a resulting hole from the separation of the pledget is limited to the size of fasteners passed through the wall of balloon 108. In some cases, pledgets 126 can be defined by weakened sections 196 of the balloon wall surrounding each pledget 126 such that detachment of each pledget 126 creates a pledget sized hole in balloon 108. In some cases, pledgets 126 can each be secured to anatomical locations prior to separation. In some cases, an inflation medium flow can be reduced or stopped prior to separation.

Balloon 108 of balloon catheter suturing system 100 can be a weeping balloon. Weeping balloon, in the context of the present disclosure, includes a balloon structure defining one or more perforations (also described as apertures or micropores, extending through a balloon wall). As such, weeping balloons can transfer inflation media through the balloon wall, from interior cavity to exterior surface of balloon 108. Transferring inflation media to exterior surface can provide a benefit of displacing blood from exterior surface of balloon 108 that would otherwise blur or obstruct visual imaging through balloon 108. In other words, inflation media transferred through the one or more perforations can help keep the exterior surface visually clear. If you just put a balloon against an anatomical surface, blood can be trapped on the balloon surface and thus obscures the view, but inflation media (e.g., saline) exiting the pores of a weeping balloon can wash away this blood on the balloon surface adjacent to the wall. In some cases, a weeping balloon used in a balloon catheter suturing system or device provided herein can have at least 3 punctured holes. In some cases, weeping balloons used in balloon catheter suturing systems or devices provided herein can have between 3 and 10,000 punctured holes, between 3 and 1,000 punctured holes, between 3 and 100 punctured holes, or between 3 and 10 punctured holes. In some cases, the number and dimensions of punctured holes in a weeping balloon used in a balloon catheter suturing system or device provided herein allows for an inflation media flow rate of between 1 and 50 ml/minute. In some cases, systems and methods provided herein control an inflation media flow rate to be between 3 ml/minute and 10 ml/minute. In some cases, a weeping balloon used in balloon catheter suturing systems and devices provided herein can have hundreds of holes that perfuse inflation media (e.g., saline) through the balloon and into the blood. In some cases, a weeping balloon used in a balloon catheter suturing system or device provided herein can have a greater pore density in portions of the balloon wall in the center of the field of view and a lower pore density around a periphery of the field of view.

Figure 2:
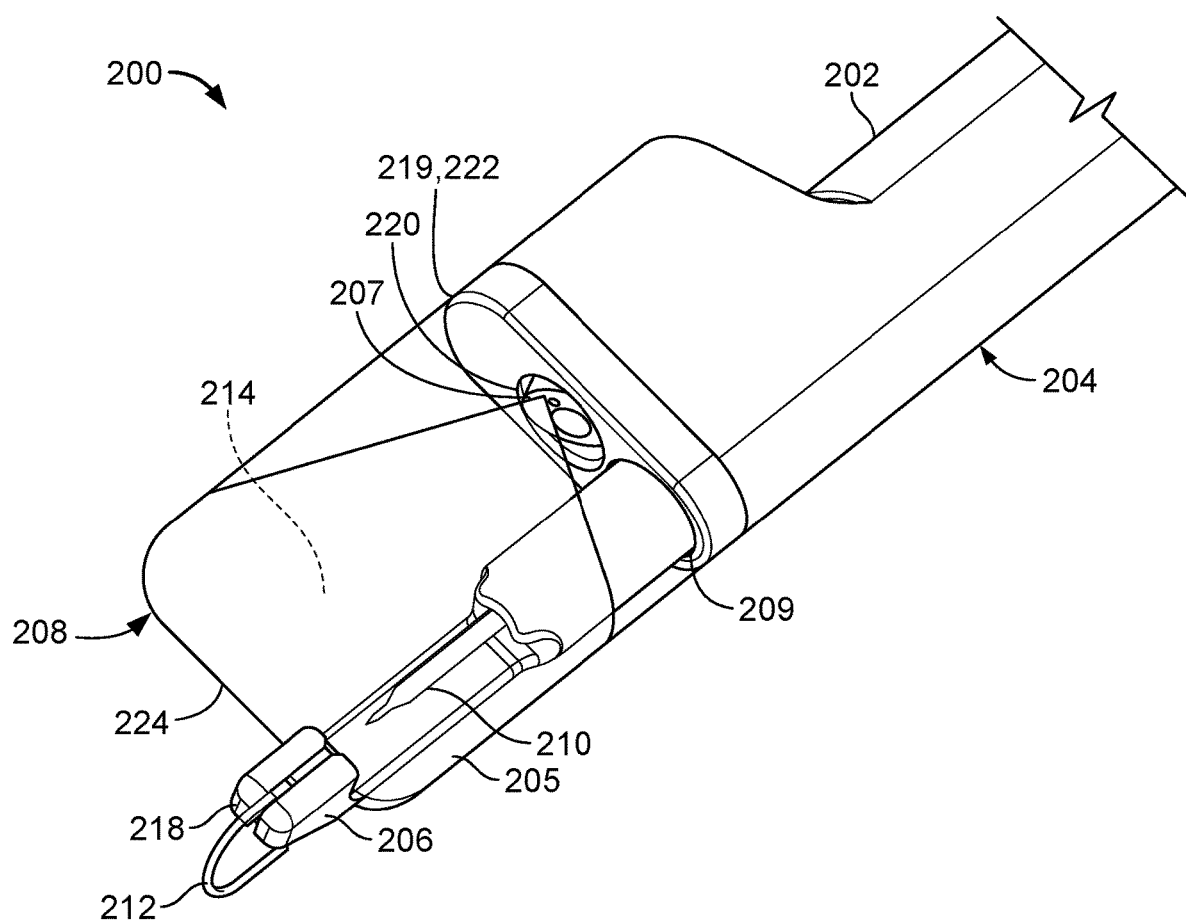
FIG. 2 is a perspective view of a distal end portion of another exemplary balloon catheter having a detachable pledget.

FIG. 2 is a perspective view of another example of a balloon catheter suturing system 200. As shown, balloon catheter suturing system 200 includes a tubular body 202 with distal end portion 204, a pledget 206, suturing thread 212, and an integrated camera 207 disposed within a balloon 208.

In FIG. 2, pledget 206 is held distal to balloon 208 by a pledget support 205 that extends adjacent the balloon 208 from a lumen 209 at a distal end 219 of tubular body 202 within balloon 208 while another portion of fastening element 206 extends adjacent to balloon 208. As shown in FIG. 2, a portion of pledget support 205 extends around and distal to balloon 208 such that pledget 206 forms a distal tip 218 of balloon catheter suturing system 200. In some cases, multiple pledgets 206 can be included. In some cases, a portion of pledget 206 can extend through the balloon 208. In some cases, a portion of pledget 206 that is disposed within interior cavity 214 can be subsequently extended through a wall of balloon 208 to an exterior environment during a medical procedure.

Balloon catheter suturing system 200 can include a fastening tool 210 adapted to penetrate tissue, separate tissue, and/or deliver a fastener 212 through the pledget and tissue, to secure a suture to tissue and/or to attach two pieces of tissues together. As shown, fastener 212 is suturing thread. In some cases, fastening tool 210 can be in the form of, for example, a needle, knife, scalpel, cutter and combinations thereof. In some cases, staple, hook, tack, clamp, a clip, or other suturing devices can be used instead of or with suturing thread 212.

As shown in FIG. 2, integrated camera 207 is disposed at the distal end 219 of tubular body 202 to provide visual imaging of a patient's anatomy during the medical procedure. Camera 207 may be fully or partially disposed within a lumen 220 defined by tubular body 202. The camera can be coupled to electrical and/or optical cables (not shown) in lumen 220 that extend longitudinally through tubular body 202 towards a proximal end portion of tubular body 202. In some cases, camera 207 is electrically connected to the external electronics with wires through lumen 220. In some cases, a bundle of fiber optic cables, each with their own lens (e.g., borescopes), can be connected to an eyepiece for viewing or a camera for electrical conversion and transfer to a screen. In some cases, camera 207 includes externally powered but internal LEDs to emit light so that the tissue can be seen. In some cases, systems provided herein have optical fibers and an external light source.

A rectangular-shaped balloon 208, as shown in FIG. 2, can be coupled to distal end 219 of tubular body 202. In FIG. 2, balloon 208 has a proximal end 222 and a distal end 224. Balloon 208 can define an interior cavity 214 that extends between proximal and distal ends 222, 224. Balloon 208 can be expanded by filling interior cavity 214 with an inflation media, such as saline solution.

Balloon 208 of balloon catheter suturing system 200 can be a weeping balloon. Weeping balloon, in the context of the present disclosure, includes a balloon structure defining one or more perforations (also described as apertures or micropores, extending through a balloon wall). As such, weeping balloons can transfer inflation media through a balloon wall, from interior cavity 214 to exterior surface of balloon 208. Transferring inflation media to exterior surface can provide a benefit of displacing blood from exterior surface of balloon 208 that would otherwise blur or obstruct visual imaging through balloon 208. In other words, inflation media transferred through the one or more perforations can help keep the exterior surface visually clear. If you just put a balloon against an anatomical surface, blood can be trapped on the balloon surface and thus obscures the view, but inflation media (e.g., saline) exiting the pores of a weeping balloon can wash away this blood on the balloon surface adjacent to the wall. In some cases, a weeping balloon used in a balloon catheter suturing system or device provided herein can have at least 3 punctured holes. In some cases, weeping balloons used in balloon catheter suturing systems or devices provided herein can have between 3 and 10,000 punctured holes, between 3 and 1,000 punctured holes, between 3 and 100 punctured holes, or between 3 and 10 punctured holes. In some cases, the number and dimensions of punctured holes in a weeping balloon used in a balloon catheter suturing system or device provided herein allows for an inflation media flow rate of between 1 and 50 ml/minute. In some cases, systems and methods provided herein control an inflation media flow rate to be between 3 ml/minute and 10 ml/minute. In some cases, a weeping balloon used in balloon catheter suturing systems and devices provided herein can have hundreds of holes that perfuse inflation media (e.g., saline) through the balloon and into the blood. In some cases, a weeping balloon used in a balloon catheter suturing system or device provided herein can have a greater pore density in portions of the balloon wall in the center of the field of view and a lower pore density around a periphery of the field of view.

Figure 3A:
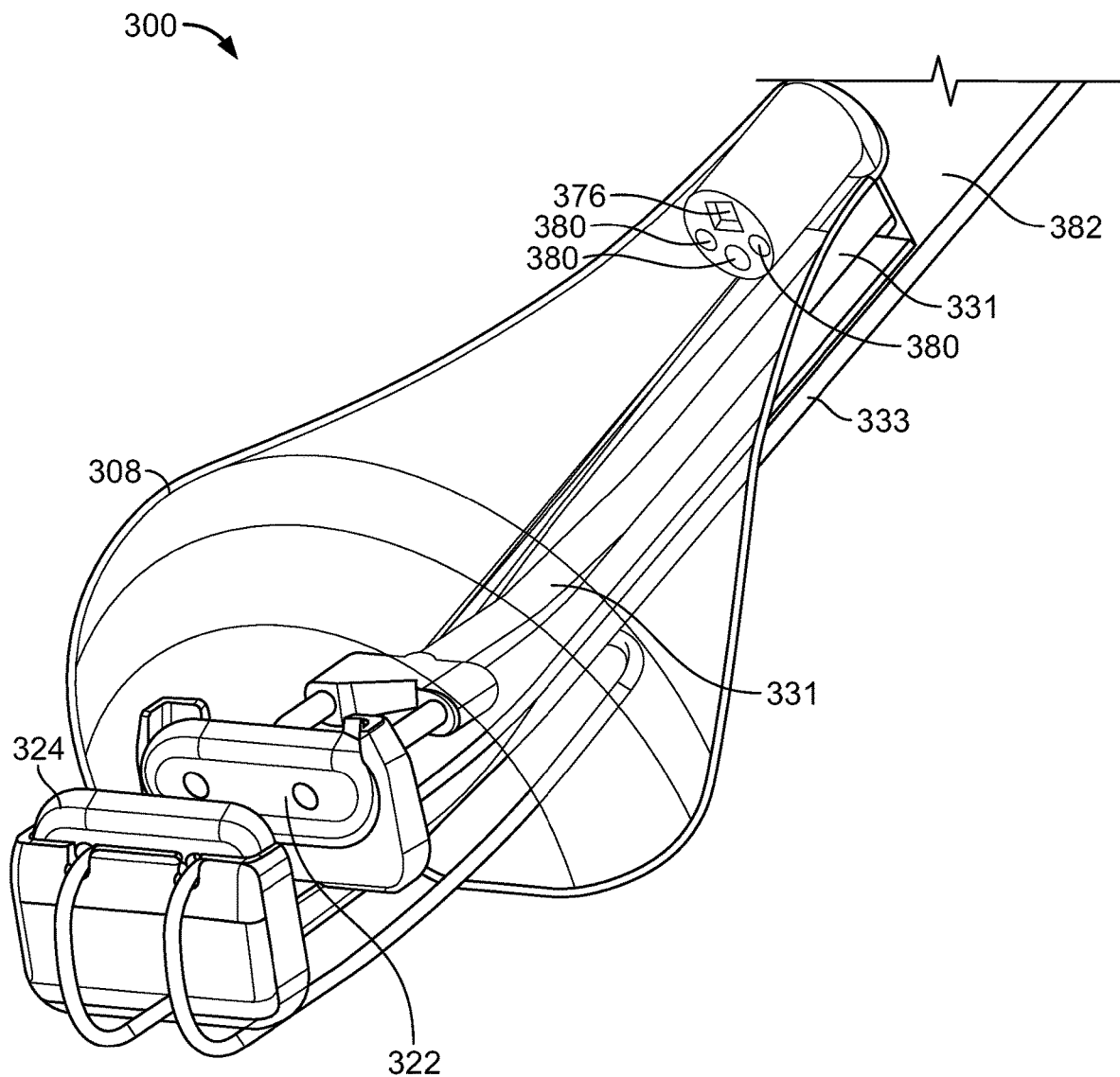
FIGS. 3A-3J depict another exemplary balloon catheter suture delivery system having a pair of pledgets disposed distal to the balloon.
Figure 3B:
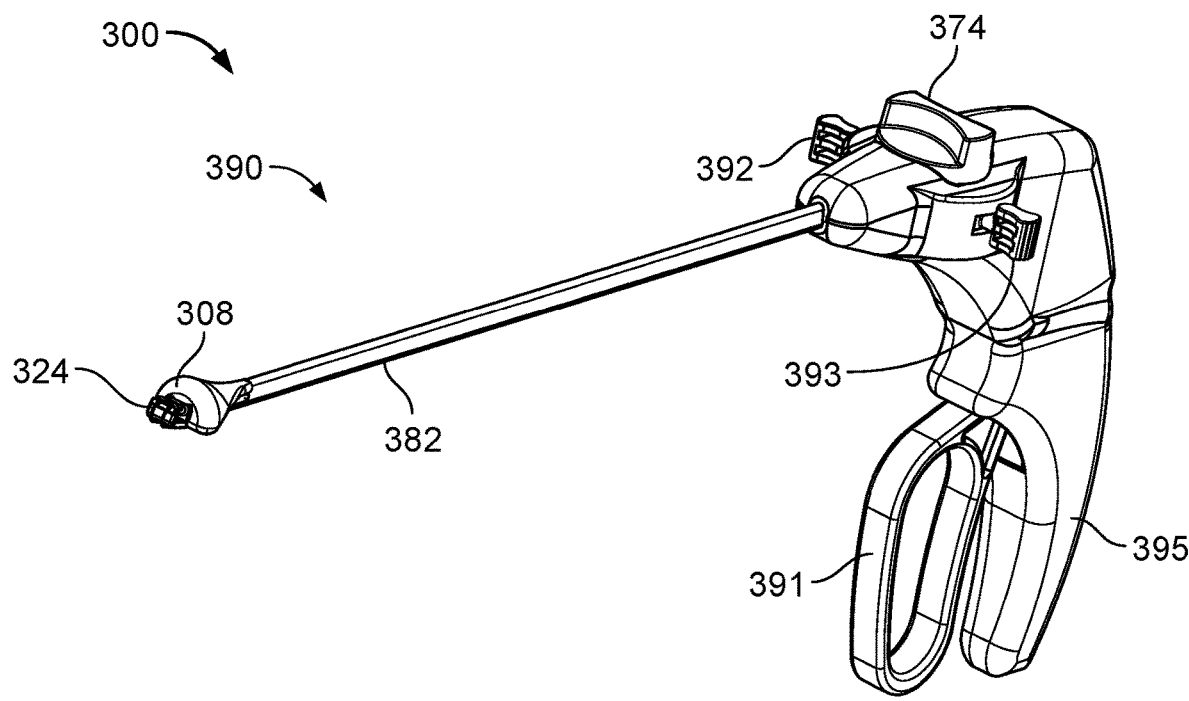
Figure 3C:
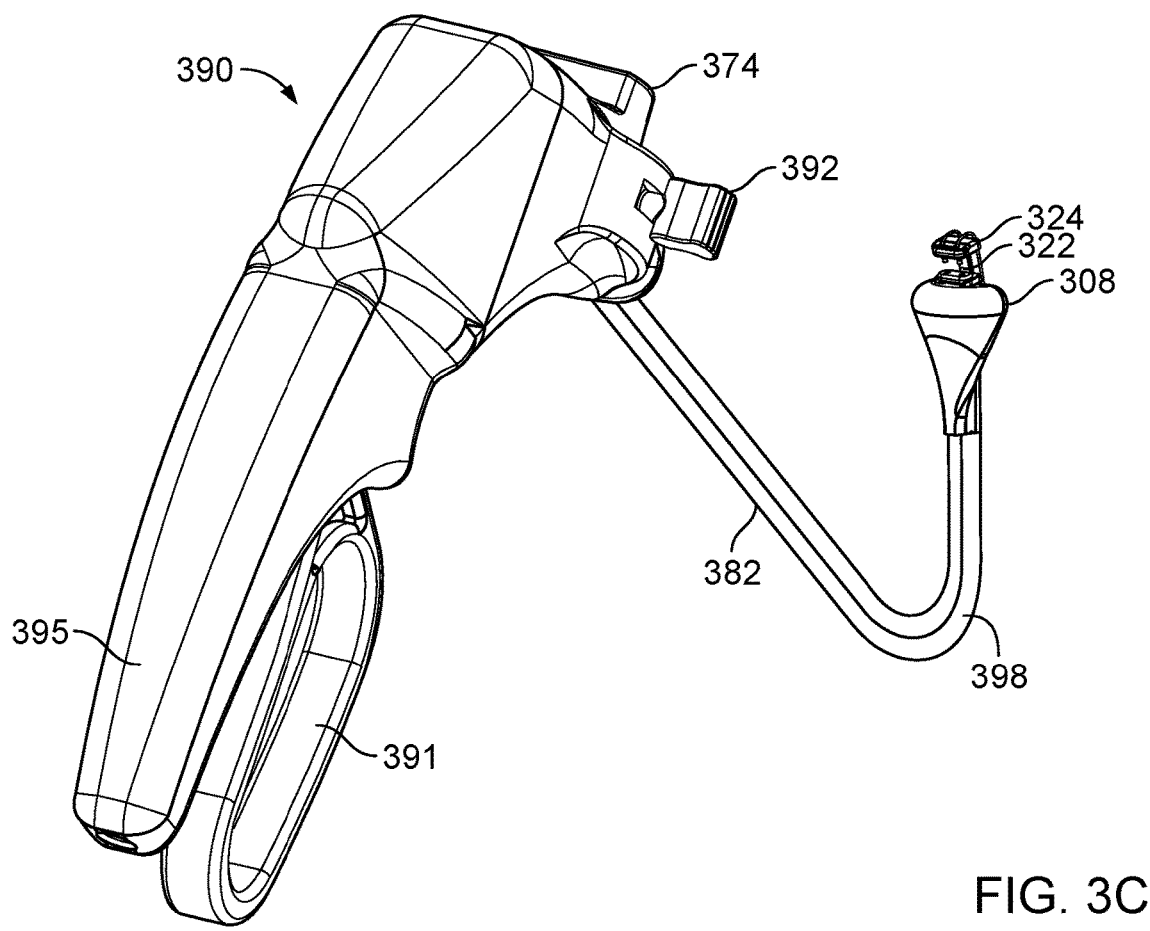

FIGS. 3A-3J depict another exemplary balloon catheter suture delivery system 300 having a pair of pledgets 322 and 324 disposed distal to balloon 308. FIG. 3A depicts a distal end of system 300. FIGS. 3B and 3C depict a controlling handle for the system. FIGS. 3D-3I depict system 300 being used to suture the valve annulus 301 of a tricuspid valve.

Figure 3D:
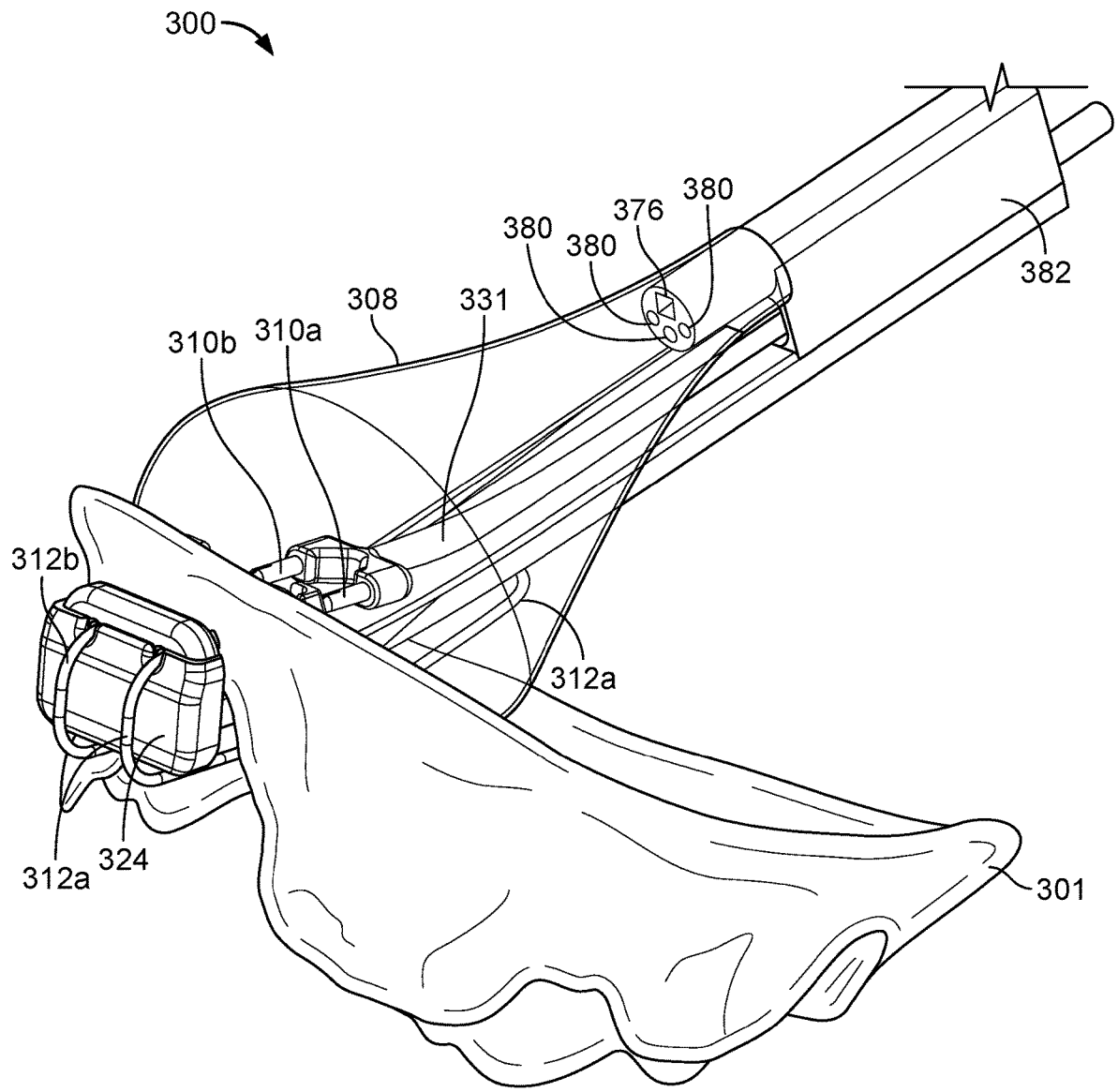
Figure 3E:
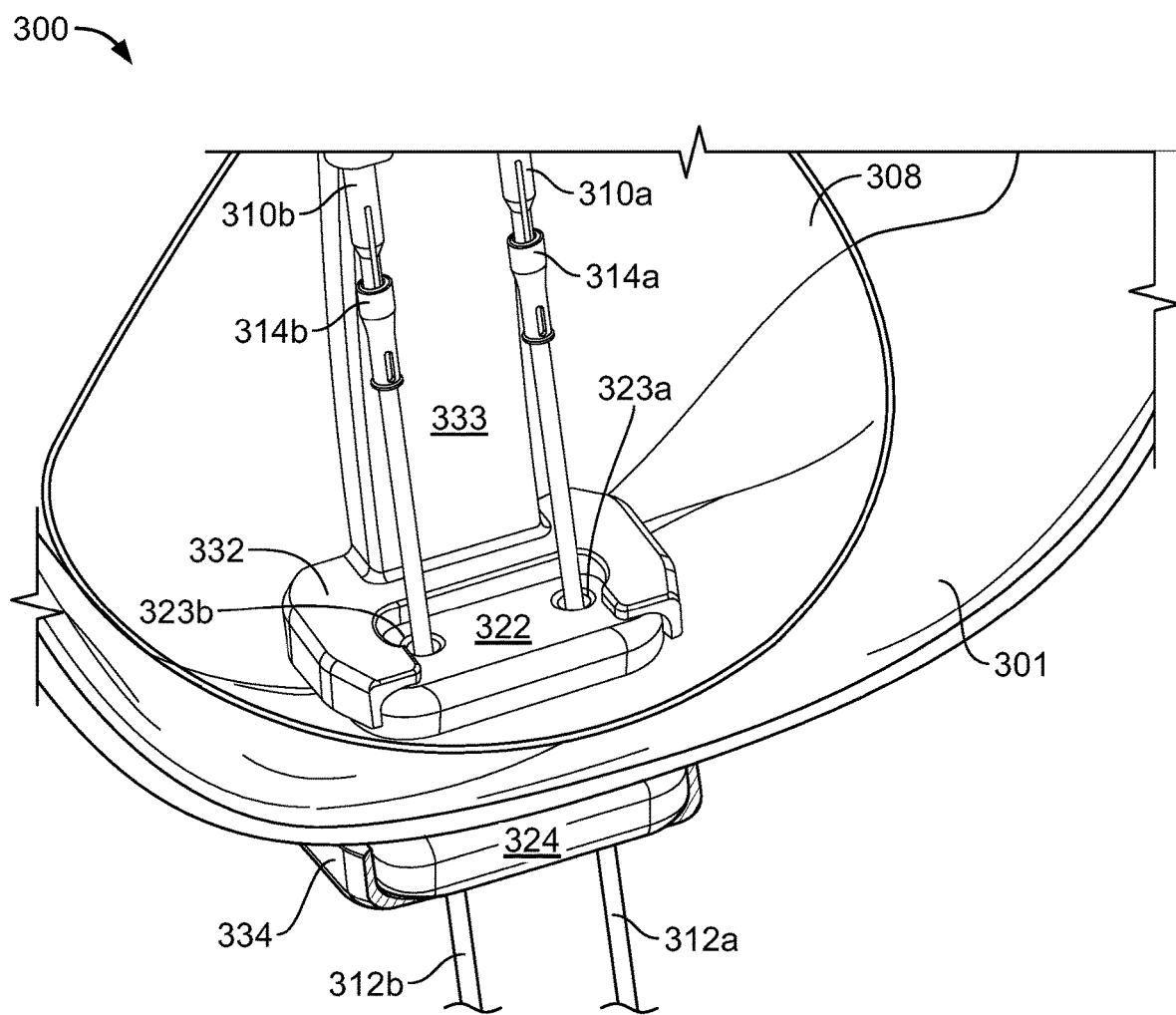
Figure 3F:
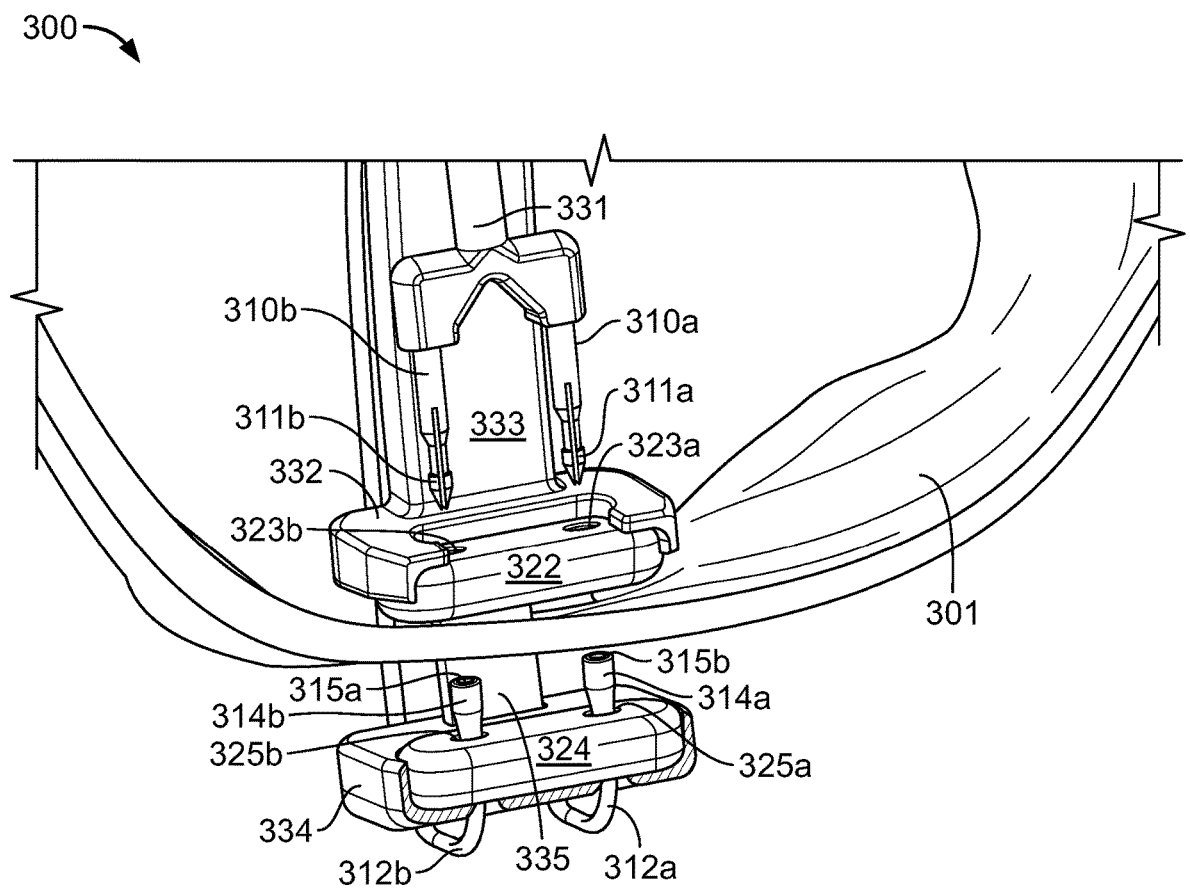
Figure 3G:
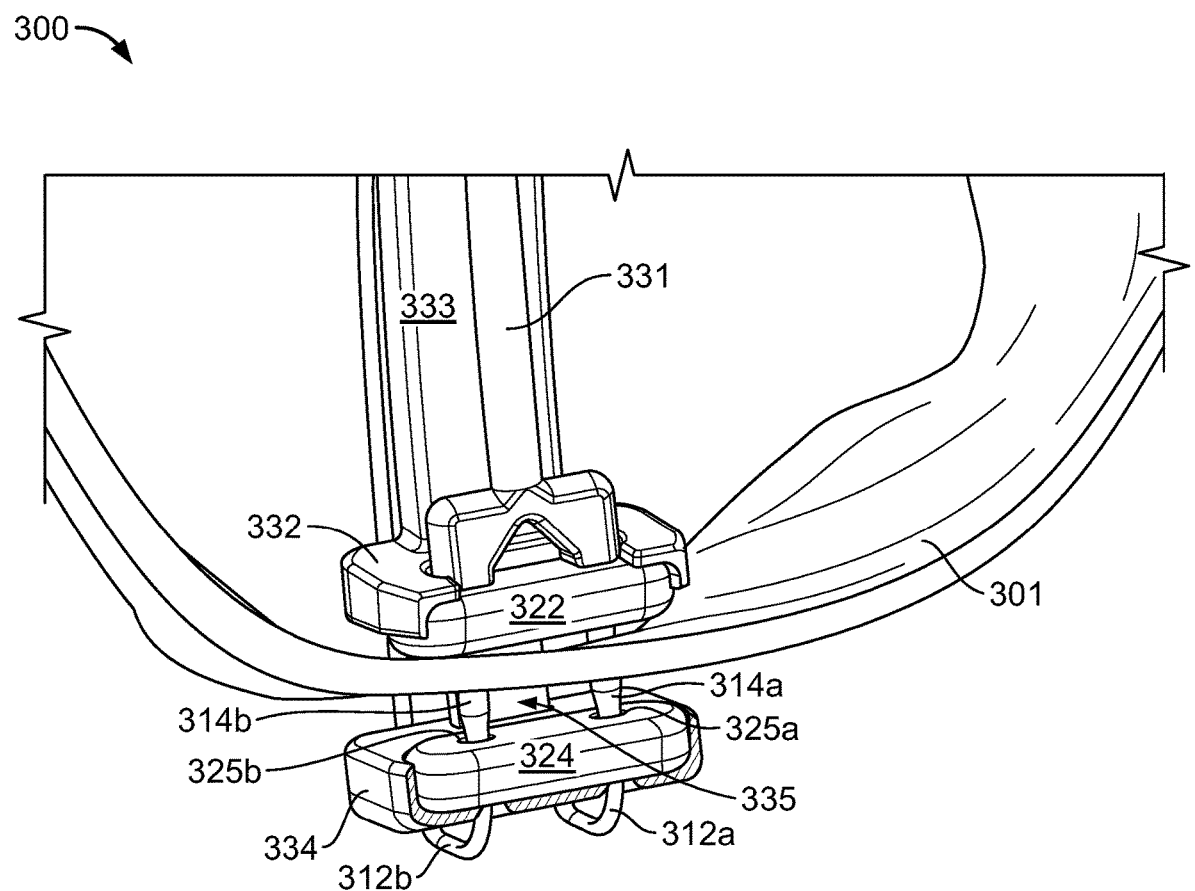
Figure 3H:
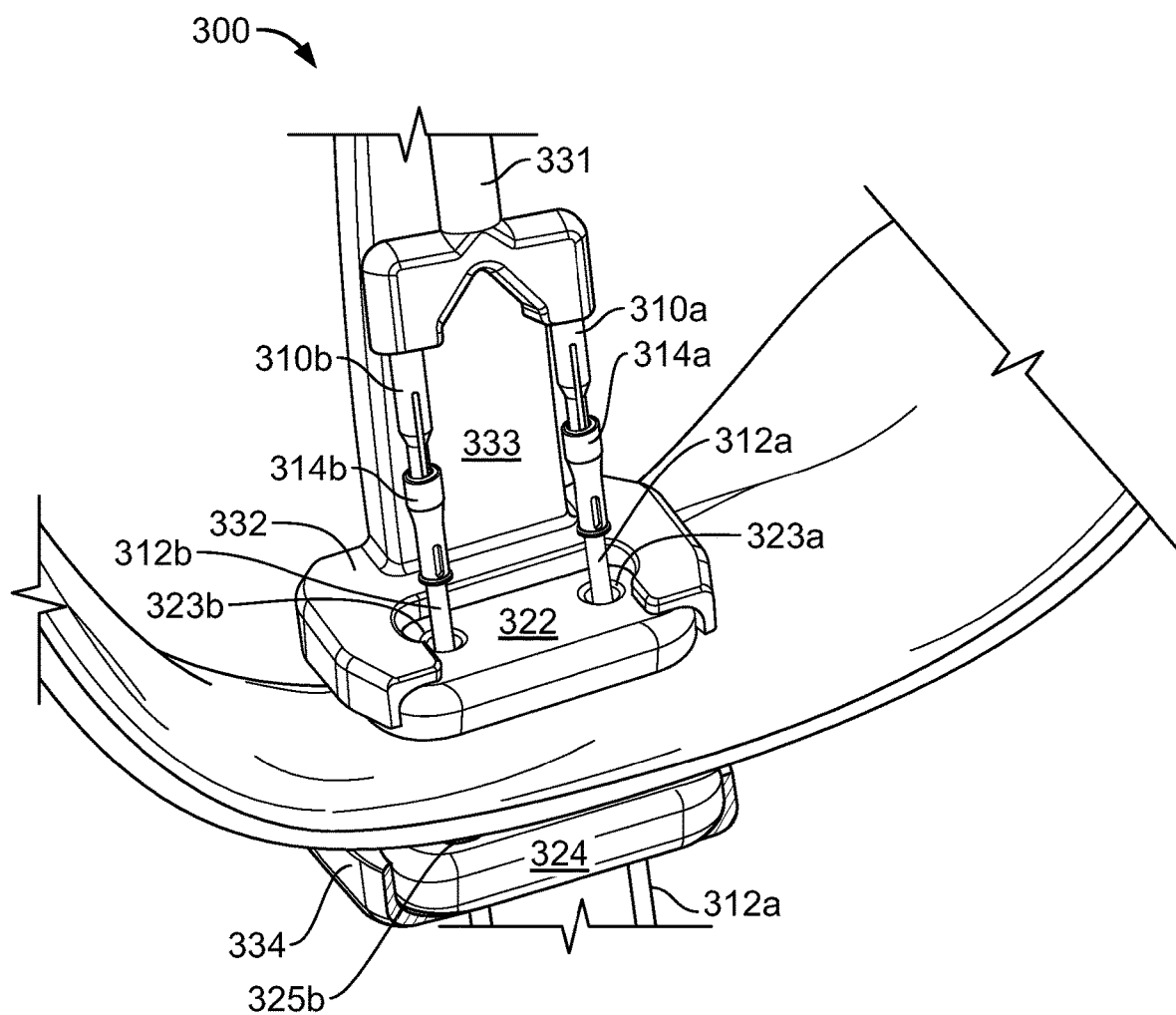
Figure 3I:
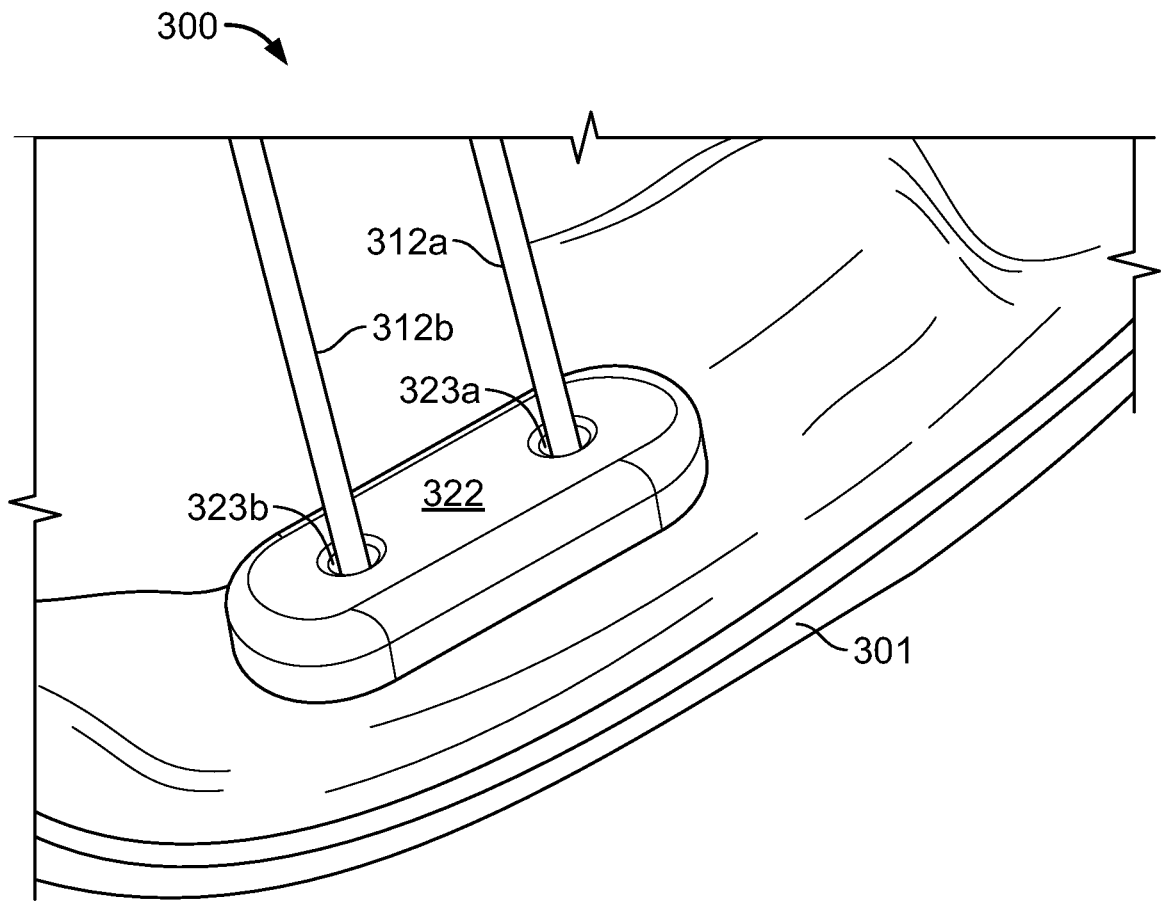
Figure 3J:
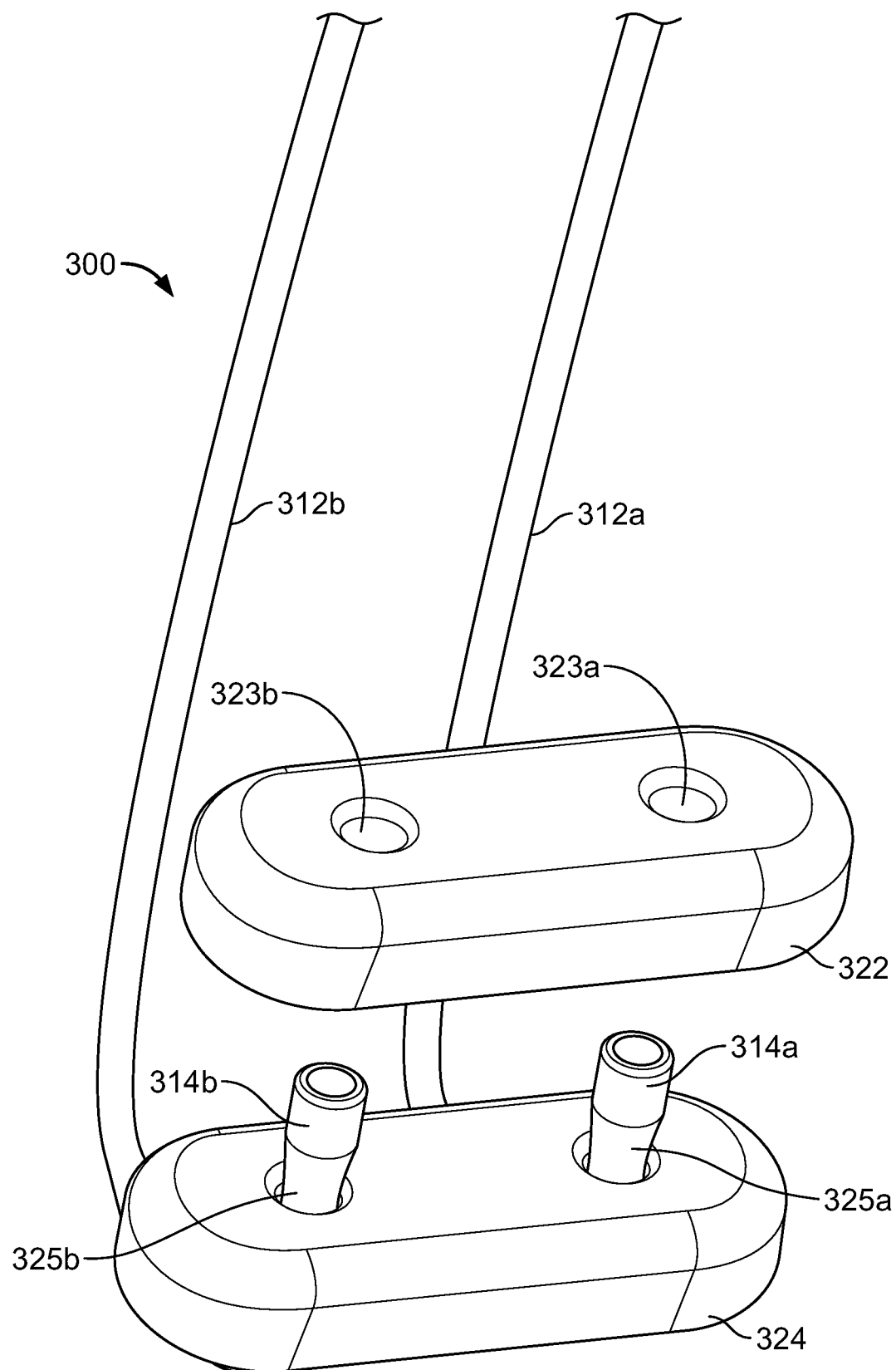

As shown in FIG. 3A, balloon catheter suturing system 300 includes an inner pledget 322 and an outer pledget 324. Inner pledget 322, as shown in FIG. 3E, is held adjacent to a distal end of balloon 308 by an inner pledget support structure 332, which can extend through a channel formed in balloon 308, and outer pledget 324 is held distal to inner pledget 322 by an outer pledget support structure 334. As shown in FIG. 3C, balloon catheter suturing system 300 can be manipulated by a controlling handle 390 to position a distal end of system 300 as desired. As shown in FIGS. 3D-3I, the distal end can be manipulated to position tissue 301 (e.g., a valve annuals of the tricuspid valve) between inner pledget 322 and outer pledget 324 such that tissue 301 to be sutured there between. FIG. 3D depicts balloon catheter suturing system 300 after placement, but before suturing. FIG. 3E depicts system 300 after suturing threads 312a and 312b have been pulled through tissue 301 and inner pledget apertures 323a and 323b. FIGS. 3F-3H discussed below show how this is accomplished, but do not show balloon 308 in order to more clearly show steps. FIGS. 3I and 3J depict pledgets 322 and 324, suturing threads 312a and 312b, and suturing attachments, needle shuttles 314a and 314b, in isolation.

FIGS. 3D and 3F depict inner pledget 322 placed on one side of tissue 301 and outer pledget 324 positioned on an opposite of tissue 301 prior to suturing of tissue 301. As discussed above, balloon 308 is omitted from FIG. 3F for clarity. Although FIGS. 3A and 3D depict inner pledget 322 as being external to balloon 308 with inner pledget support structure 332 and internal pledget support shaft 333 extending through a working channel in balloon 308, some systems provided herein can have a balloon enclose inner pledget 322, internal pledget support structure 332, internal pledget delivery shaft 333, and fastener tool 331. Outer pledget 324, outer pledget support structure 334, outer pledget delivery shaft 335, suturing threads 312a and 312b, and needle shuttles 314a and 314b. Suturing threads 312a and 312b can be positioned such that they extended through outer pledget apertures 325a and 325b prior to delivery of balloon catheter suturing system 300 and retained in outer pledget apertures 325a and 325b by needle shuttles 314a and 314b, which can have a larger outer diameter than the inner diameter of outer pledget apertures 325a and 325b. Needle shuttles 314a and 314b can include stylet receiving apertures 315a and 315b adapted to lock with opposing distal anvils 311a and 311b of stylets 310a and 310b of fastener tool 331, which are supported on stylets 310a and 310b. Inner pledget support structure 332, outer pledget support 334, and fastener tool 331 can be moved relative to each other by their respective shafts. Outer pledget support structure 334 is attached to outer pledget delivery shaft 335. As shown in FIG. 3F, inner pledget 322 and needle shuttles 314a and 314b can be spaced to allow for tissue 301 to slide there between.

FIG. 3G depicts the advancement of the fastener tool 331 such that distal anvils 311a and 311b of stylets 310a and 310b pass through inner pledget apertures 323a and 323b, such that opposing distal anvils 311a and 311b engage with stylet receiving apertures 315a and 315b of needle shuttles 314a and 314b. Opposing distal anvils 311a and 311b can have a sharp point to facilitate piercing of tissue 301. As shown, fastener tool 331 can be positioned in a working channel formed along or through balloon 308. In some cases, fastener tool 331 can be positioned within balloon 308 and stylets 310a and 310b can also pierce balloon 308 prior to passing through inner pledget apertures 323a and 323b. In some cases, balloon 308 is a weeping balloon that is resistant to tear propagation, thus balloon 308 can tolerate the formation of additional apertures formed in balloon 308 due to the passage of stylets 310a and 310b through the balloon.

FIG. 3H depicts suturing threads 312a and 312b being pulled through tissue 301, and through inner pledget apertures 323a and 323b when the fastener tool 331 (see FIG. 3G) retracts needle shuttles 314a and 314b proximally. In some cases, suturing threads 312a and 312b can additionally be pulled into balloon 308.

FIG. 3I depicts inner pledget 322 secured against tissue 301 by suturing threads 312a and 312b through holes. Outer pledget 324 is not shown in FIG. 3I, but is on an opposite side of tissue 301. Suturing threads 312a and 312b can be subsequently tied off or otherwise secured to complete the suture.

In some cases, inner pledget 322 can be positioned within balloon 308. In cases where an inner pledget 322 is positioned within balloon 308, as shown in FIG. 3E, inner pledget support structure 332 and inner pledget support shaft 333 can be positioned within balloon 308. In cases where an inner pledget 322 is positioned within balloon 308, balloon 308 can be torn or cut to be separated from inner pledget 322 after suturing. In some cases, balloon 308 can be torn or cut to be separated from the pledgets 322 and 324. In some cases, a portion of a balloon wall between pledgets 322 and 324 can rip along weakened tear lines to remain a part of the suture and an additional pledget structure. In some cases, balloon 308 can rip to be allow inner pledget 322 to be separated from balloon catheter suturing system 300.

Referring back to FIGS. 3B and 3F, balloon catheter suturing system can include a controlling handle 390 at a proximal end. Controlling handle 390 can include a handle 395, a trigger 391 for controlling the bend 398 of a tubular body 382 to control the placement of distal end of system 300. Levers 392 and 393 and knob 374 can control the advancement and/or retraction of the fastener tool 331, inner pledget support shaft 333, and outer pledget support shaft 335. Levers 392 and 393 and knob 374 can also control the tying of suture threads 312a and 312b. In some cases, inner pledget support shaft 333 is integral with tubular body 382 such that levers 392 and 393 control the movement of the fastener tool 331 and the outer pledget support shaft 335 relative to the tubular body 382 and the inner pledget support shaft 333. In some cases, knob 374 can be used to manipulate fastener tool 331 to tie suturing threads 312a and 312b together.

Referring to FIGS. 3A and 3D again, a distal end of system 300 can include a plurality of channels 380 for delivery of inflation media, tools, fiber optics, cameras, etc. in tubular body 382. In some cases, a camera 376 can be integrated into shaft tubular body 382.

Figure 4:
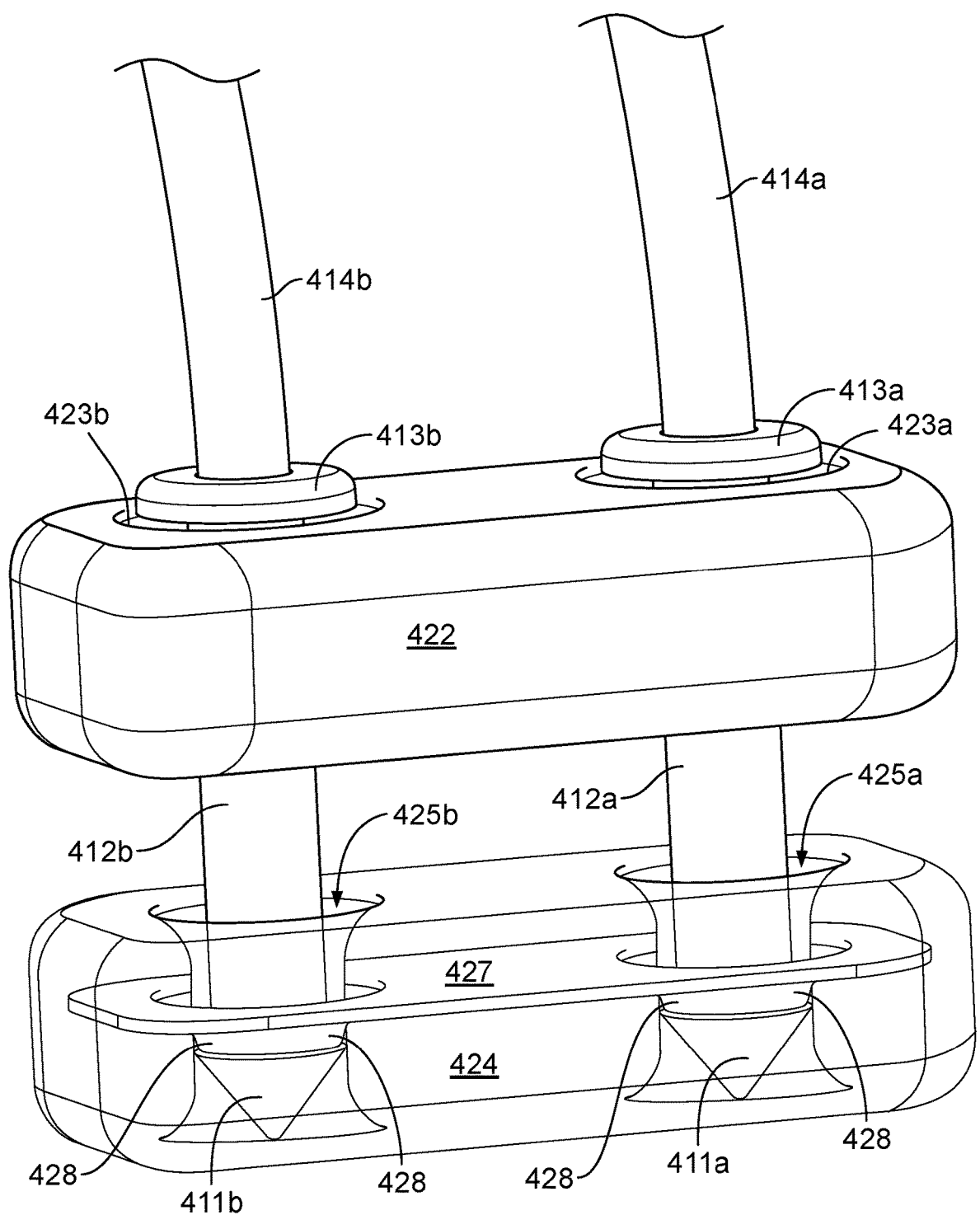
FIG. 4 depicts another exemplary suture system that can be used with a balloon catheter suture delivery system provided herein.

FIG. 4 depict another exemplary suture system that can be used with a balloon catheter suture delivery system provided herein. The suture system of FIG. 4 has stylet fasteners 412a and 412b for suturing tissue (e.g., a valve annulus of a tricuspid valve) in between an inner pledget 422 and an outer pledget 424. A balloon catheter suturing system provided herein can have a structure is similar to balloon catheter suturing system 300 depicted in FIGS. 3A-3I, but uses the suturing system of FIG. 4 to suture tissue to inner pledget 422 and outer pledget 424.

Inner pledget 422 can include inner pledget apertures 423a and 423b, which hold fasteners 412a and 412b. Fasteners 412a and 412b can be stylet fasteners having proximal anvils 413a and 413b and distal anvils 411a and 411b. Proximal anvils 413a and 413b can rest on an upper surface of inner pledget 422 to prevent stylet fasteners 412a and 412b from passing entirely through apertures 423a and 423b. Distal anvils 411a and 411b are adapted to be received and locked into outer pledget apertures 425a and 425b in outer pledget 424. Stylet fasteners 412a and 412b can be advanced to pierce tissue and insert the distal anvils into the outer pledget apertures 425a and 425b by advancing an inner pledget support structure, which can cover at least a portion of proximal anvils 413a and 413b. Wires 414a and 414b can be releasably secured to proximal anvils 413a and 413b to hold the stylet fasteners 412a and 412b against an inner pledget support structure. FIG. 4 depicts inner pledget 422 and stylet fasteners 412a and 412b that can be advanced through tissue and distal anvils 411a and 411b that can be pushed into outer pledget apertures 425a and 425b. Accordingly, an inner pledget support structure and inner pledget support shaft act as a suturing tool.

FIG. 4 shows internal locking structures 428 within external apertures 425a and 425b and how they lock distal anvils 411a and 411b of stylet fasteners 412a and 412b. Outer pledget 424 can include an internal plate 427. In some cases, pledget 424 can be formed by injection molding a polymeric material around plate 427. Plate 427 includes two plate apertures surrounded by locking structures 428, which can clasp and lock distal anvils 411a and 411b. Distal anvils 411a and 411b can be conical to push locking structures out as distal anvils 411a and 411b are pressed against locking structures 428 until a bottom edge of the conical tip passes a lower edge of locking structures 428, which results in locking structures 428 snapping against a shaft of stylet fasteners 412a and 412b. A bottom edge of the conical tip thus acts as a mechanical stop that locks the distal anvil from be retracted out of outer pledget apertures 425a and 425b. After the pledgets 422 and 424 are secured together on opposite sides of tissue, wires 414a and 414b can be retracted from proximal anvils 413a and 413b.

Balloons used in the balloon catheter suturing systems of FIGS. 1A-4F can use any suitable balloon shape. As discussed above, in some cases, pledgets are held external to the balloons. In some cases, balloons can include one or more working channels for one or more tools (e.g., pledget support shafts, fastening tool, etc.) to access an anatomical structure (e.g., a tricuspid valve). In some cases, a working channel can have a balloon extend along three sides of the channel. In some cases, a working channel can be surrounded by a donut-shaped balloon. In some cases, balloons used in balloon catheter suturing systems 100, 200, or 300 can include tools within the balloon. In some cases, tools within the balloon can pass through the balloon wall to access anatomical structures. In some cases, a pledgets can be a part of the balloon wall, can be located within a balloon, or held adjacent an outer surface of the balloon. FIGS. 5A-5F depict exemplary balloon shapes 500, 520, 540, 560, 580, and 590, which can be used in balloon catheter suturing devices and systems provided herein. Although not specifically shown in FIGS. 5A-5D, each of these balloon shapes 500, 520, 540, and 560 can include side working channels and/or through working channels.

Figure 5A:
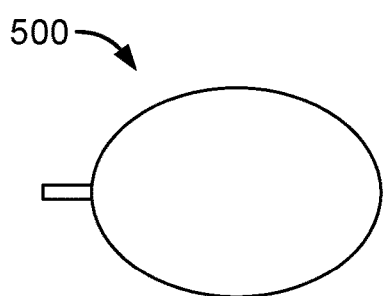
FIGS. 5A-5F show several examples of a balloon shapes that can be used in balloon catheter suturing devices and systems provided herein.
Figure 5C:
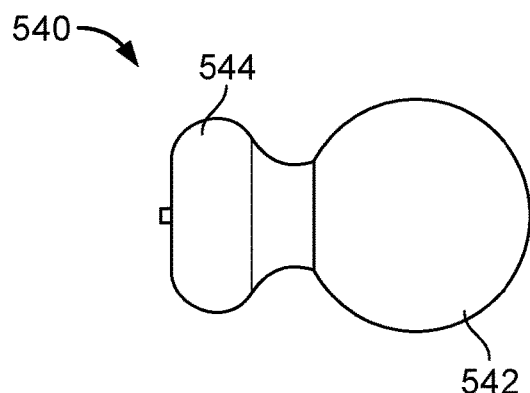
Figure 5B:
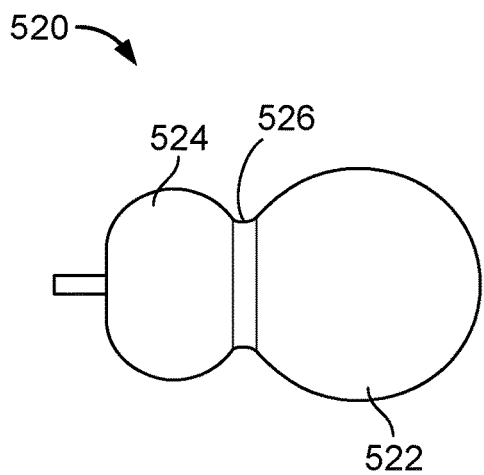
Figure 5D:
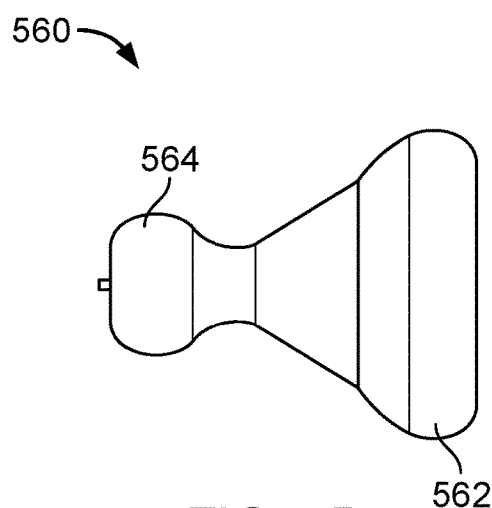
Figure 5E:
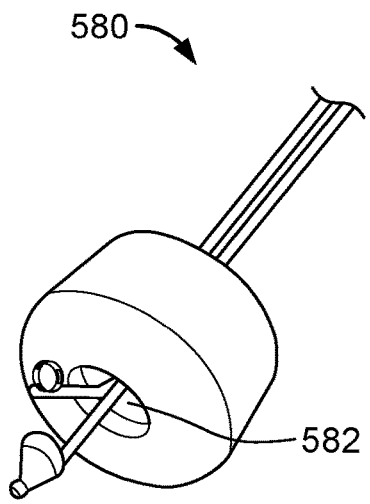
Figure 5F:
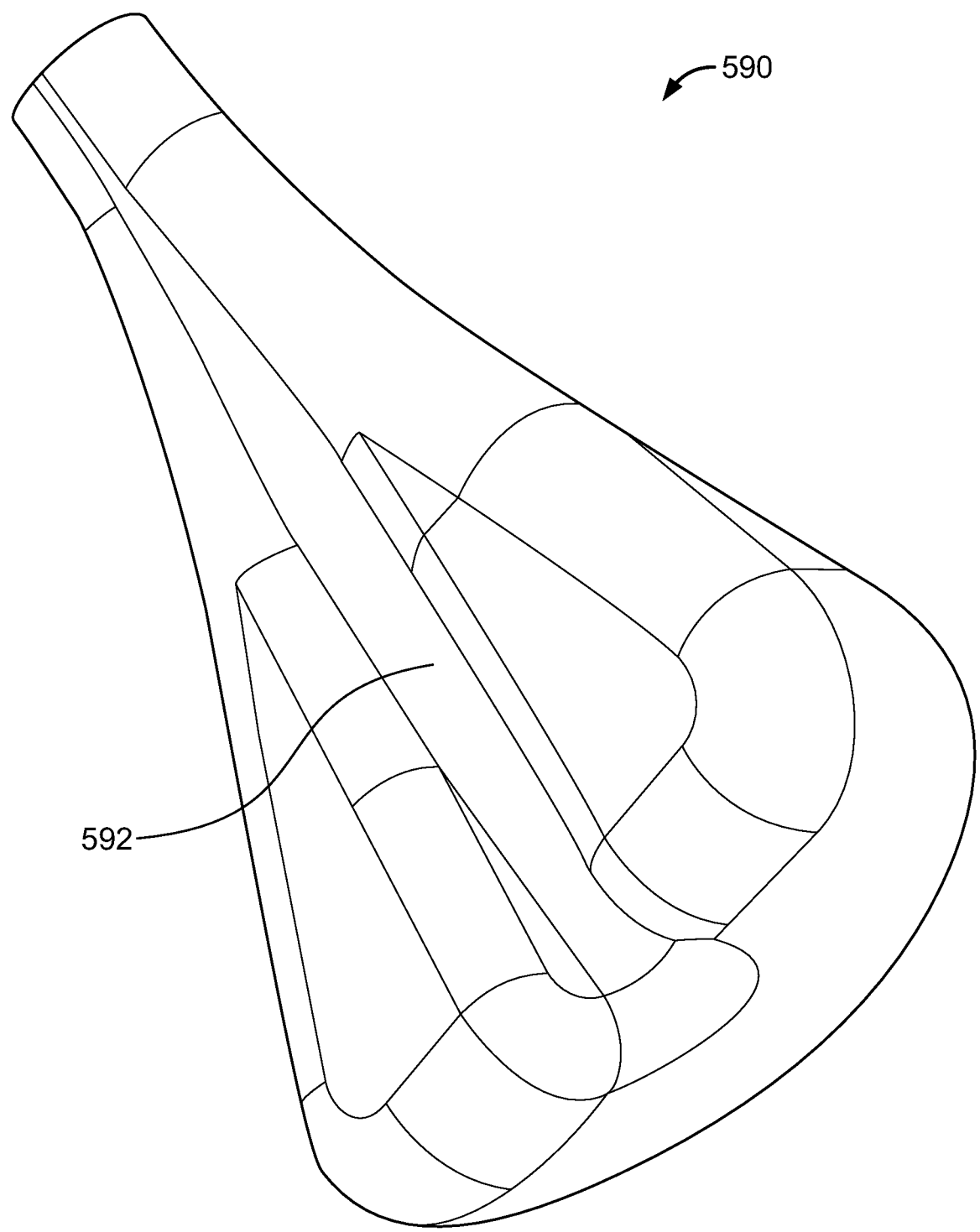

Balloons can be constructed from various forms, e.g., a film, sheet or tube of transparent materials. Also, balloons 500, 520, 540, 560, 580, and 590 may be formed into a variety of different shapes. FIG. 5A shows an example of a balloon 500 having a generally oval shape. FIG. 5B provides an example of a balloon 520 having a proximal spherical portion 522 and a distal spherical portion 524 with a necked portion 526 there between. FIG. 5C provides an example of a balloon 540 having a proximal spherical portion 542 that transitions into a distal flared portion 544. FIG. 5D shows an example of a balloon 560 having a proximal conical portion 562 coupled to a distal bulbous portion 564. FIG. 5E shows an example of a donut-shaped balloon 580 having a channel or thru lumen 582. Thru lumen 582 can be sized and shaped to allow blood or other medical devices to pass through. FIG. 5F shows an example of a half-flask shaped balloon 590 having a side working channel 592. In some cases, balloons used in balloon catheter suturing devices and systems provided herein have a diameter of between 0.5 cm to 4 cm. In some cases, balloons used in balloon catheter suturing devices and systems provided herein have a diameter of between 1.0 cm to 2 cm. In some cases, balloons used in balloon catheter suturing devices and systems provided herein can provide a field of view of between 0.5 cm to about 3 cm. In some cases, balloons used in balloon catheter suturing devices and systems provided herein can provide a field of view of between 1.0 cm to about 2.0 cm. In some cases, balloons used in balloon catheter suturing devices and systems provided herein can provide a field of view of about 1.5 cm. In some cases, the ratio of longitudinal balloon length versus diameter is approximately 1:1 with the camera's angle of view being about 30 degrees.

Balloon 500, 520, 540, 560, 580, and 590 can be a compliant balloon that fills with an inflation media, which inflates balloon from a smaller deflated size to a larger inflated size thus allowing a larger device to be transferred through the catheter. Balloon 500, 520, 540, 560, 580, and 590 can be adapted to be filled with inflation media supplied through one or more lumens of a tubular body, e.g., tubular body 112 of FIG. 1, from a fluid source that connects to a manifold at a proximal end of tubular body 112. In some cases, balloon 500, 520, 540, 560, 580, and 590 can be filled with inflation media, e.g., saline solution, to facilitate visualization through camera, e.g., camera 207 of FIG. 2, at a distal end portion of a direct visualization catheter. Balloon 500, 520, 540, 560, 580, and 590 can facilitate visualization in several ways. In some cases, balloon 500, 520, 540, 560, 580, and 590 can be used to visualize anatomical features within the anatomy when pressed against a targeted anatomical feature and inflation media flows out of pores to clear an exterior surface of balloon of blood. In some cases, balloon 500, 520, 540, 560, 580, and 590 can be composed of materials that are optically transparent when exposed to a particular inflation media and/or bodily fluids.

Balloon 500, 520, 540, 560, 580, and 590 as well as other medical device components, can be constructed of various materials that are optically transparent when exposed to inflation media, e.g., saline solution, and/or bodily fluids, e.g., blood. In some cases, balloon 500, 520, 540, 560, 580, and 590 can be constructed of various transparent materials that maintain transparency within the body over a desired duration. For example, suitable balloon materials can have anti-fouling properties, e.g., materials resistant to protein-binding and platelet adsorption, which maintain transparency over longer durations than materials that are do not have anti-fouling properties. The term "fouling" generally refers to a material that undesirably accumulates foulants, such as biomacromolecules, microorganisms, hydrocarbons, particles and colloids, from the surrounding environment. Anti-fouling properties, also referred to as a "stealth effect," reduces intermolecular forces of interactions between foulants and the balloon material. In some cases, such as in implantable applications, balloon materials can have anti-thrombogenic properties to prevent the formation of clots in the body. In some cases, balloon 500, 520, 540, 560, 580, and 590 can include a hydrophilic material. Hydrophilic materials can allow the saline to preferentially be wet over allowing the air to contact the surface. In some cases, any air bubble which may occur in the balloon can be flushed out of the field of view or broken up.

Balloon 500, 520, 540, 560, 580, and 590 may be constructed of various materials having physical, mechanical or functional properties that can improve device performance. Furthermore, these various materials can be incorporated at specific locations of the balloon where specific functional properties are desired. For example, balloon 500, 520, 540, 560, 580, and 590 can be constructed of various materials that are self-healing. Self-healing refers to a structural ability of a material, e.g., fiber-reinforced polymers, to repair mechanical damage. In another example, balloon 500, 520, 540, 560, 580, and 590 may be constructed of various materials having suitable mechanical properties, such as tensile strength, ductility and elastic modulus. In some cases, at least a portion of a balloon material can have a Shore A hardness of 90 or less to provide the balloon with suitable flexibility. In another example, balloon 500, 520, 540, 560, 580, and 590 can be constructed of various materials having suitable lubricity. Lubricity can help facilitate proper balloon placement within the anatomy and minimize blood vessel and tissue damage otherwise caused by balloon 208 or alternative medical devices.

Figure 6A:
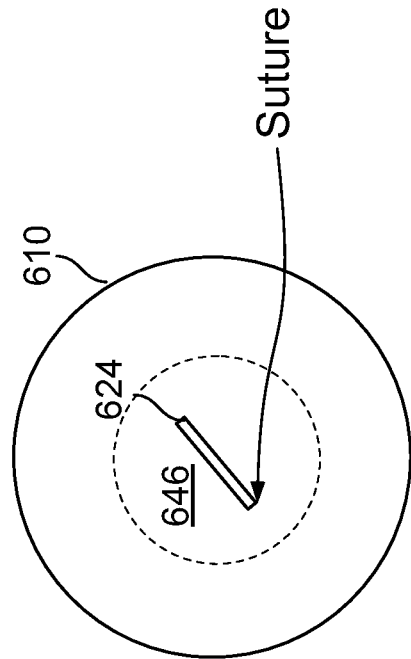
FIGS. 6A-6D depict how an exemplary balloon catheter suturing system provided herein can be used to suture tissue and leave a pledget.
Figure 6B:
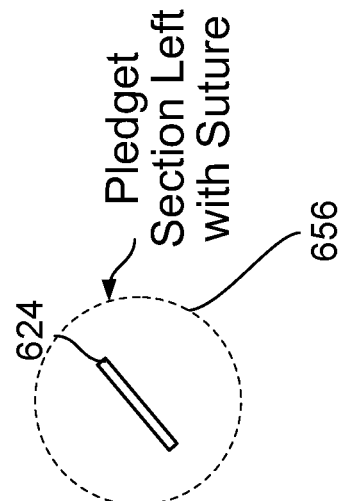
Figure 6C:
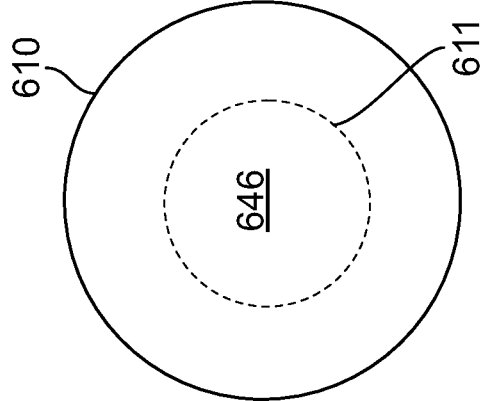
Figure 6D:
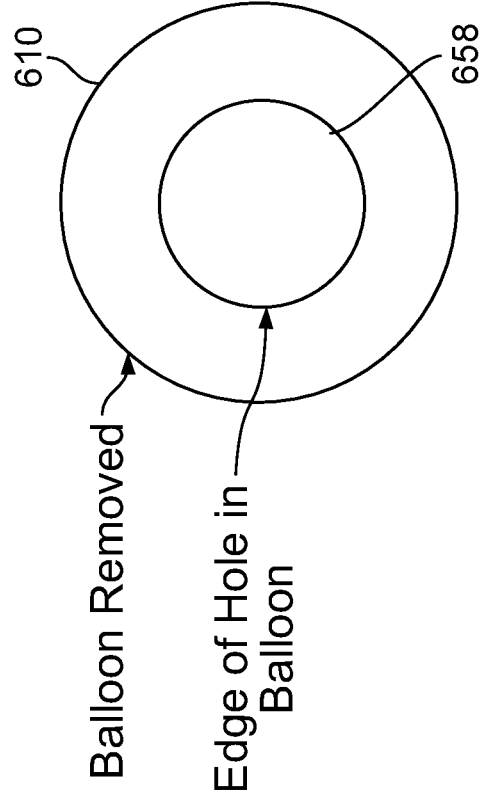

FIGS. 6A-6D depict an exemplary balloon camera view of a balloon 610 including a pledget section 646 in a balloon wall 611 defined by tear off notches in the balloon wall. FIG. 6A depicts the balloon 610 prior to having a fastener 624 (e.g., a staple or a suture) passed through the pledget section 646 and into tissue surrounding the pledget detachable section 646. FIG. 6B depicts the balloon 610 having pledget detachable section 646 sutured by fastener 624 (e.g., a staple or a suture) to tissue on an exterior surface of the pledget detachable section 646. FIG. 6C shows the balloon 610 having a hole 658 from where the pledget detachable section 646 was removed, and FIG. 6D depicts the sutured pledget 656.

Figure 8B:
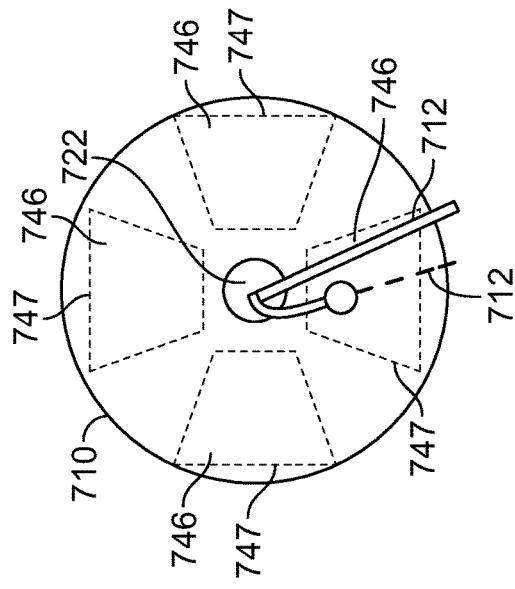
Figure 8A:
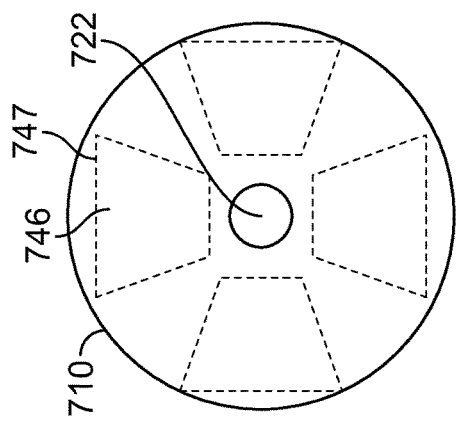
Figure 8C:
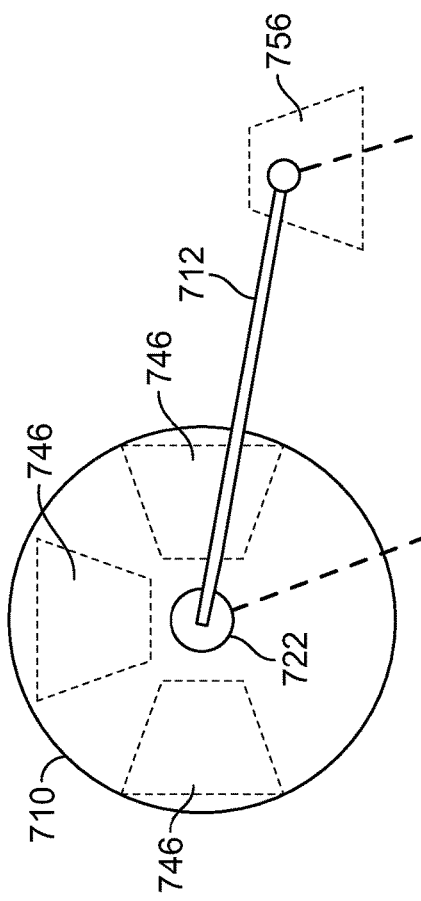

FIGS. 7A-7C illustrate a camera view showing how detachable sections 746 can be sutured to an anatomical location and separated from balloon 710. FIGS. 8A-8C depict a view of this procedure from a position distal to the balloon. As shown in FIGS. 7A and 8A, a balloon 710 can include pledget detachable sections 746 and a through working channel 722, through which a suturing thread rides with a fastening tool (not shown). The fastening tool working channel 722 can be a central hole or pore in balloon 710. As shown in FIG. 7A, each pledget detachable section 746 includes tear notches 747. As shown in FIGS. 7B, 7C, 8B and 8C, a suture thread 712 can be passed into working channel 722 by a fastening tool (not shown), piercing tissue outside of balloon 710 and piercing pledget detachable section 746 of the wall of balloon. In some cases, as shown in FIGS. 7C and 8C, after an initial suture is made, balloon 710 can be moved or retracted to separate the sutured pledget 756 from the balloon 710. In some cases, multiple pledget detachable sections 746 are sutured to different anatomical locations prior to separating the pledget detachable sections 746 from balloon 710 to product sutured pledgets 756. In some cases, the pledget detachable sections 746 are laminated to an outer surface of the balloon wall such that removal of pledget 756 does not produce a pledget sized hole in balloon 710. In some cases, pledget detachable sections 746 are defined by a weakened score line to produce a tear line around pledget detachable sections 746.

Figure 9A:
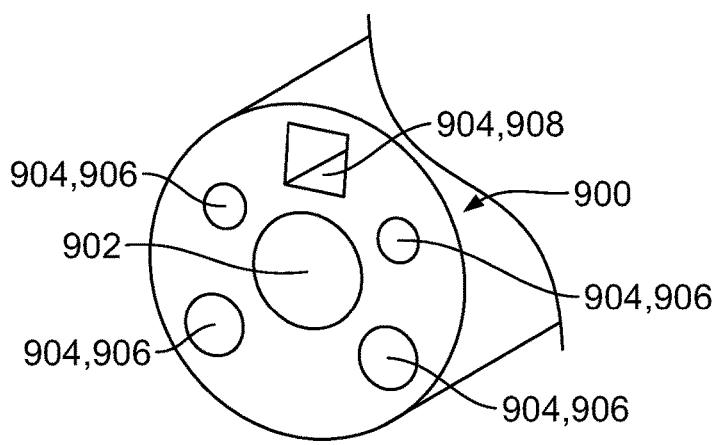
FIGS. 9A-9C show cross-sectional views of various examples of a tubular body that can be part of balloon catheter suturing devices and systems provided herein.
Figure 9B:
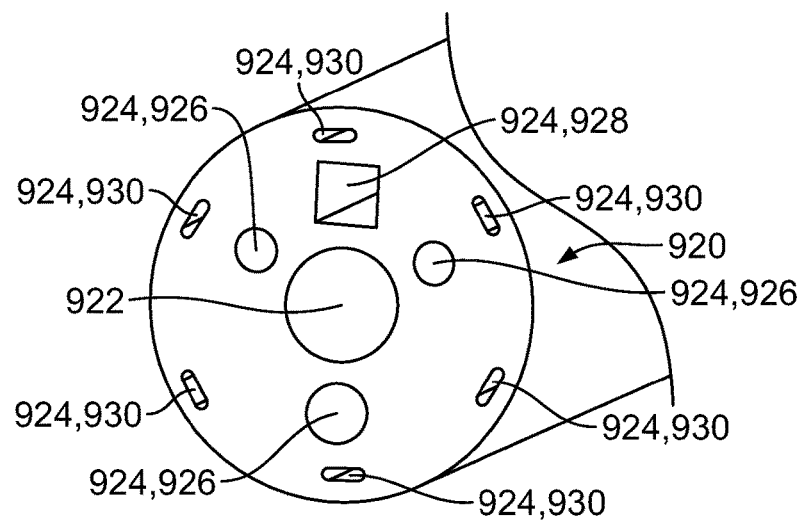
Figure 9C:
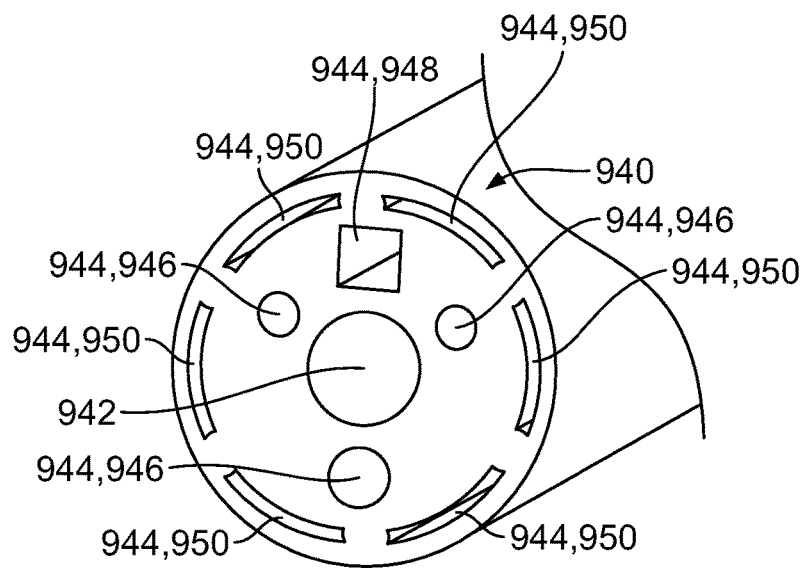

FIGS. 9A-9C show cross-sectional views of various examples of tubular bodies 900, 920, 940, which can be used in balloon catheter suturing devices and systems provided herein. In FIG. 9A, tubular body 900 includes a plurality of lumens that includes a central lumen 902 and a plurality of non-central, surrounding lumens 904. Plurality of non-central, surrounding lumens 904 of FIG. 9A includes four circular surrounding lumens 906 and one rectangular surrounding lumen 908. Central lumen and surrounding lumens can be formed of various sizes and shapes. For example, as shown in FIG. 9A, central lumen 902 can be larger than some or all non-central, surrounding lumens 904. In some cases, as shown, some of the non-central, surrounding lumens 904 can be larger than other surrounding lumens. In some cases, tubular body 900 may have only non-central, surrounding lumens 904, i.e., no central lumen. In some cases, tubular body may have one lumen or multiple lumen, for example, up to 15 lumens.

In FIG. 9B, tubular body 920 includes a plurality of lumens that includes a central lumen 922 and plurality of non-central, surrounding lumens 924. Plurality of non-central, surrounding lumens 924 of FIG. 9B includes three circular surrounding lumens 926, one rectangular surrounding lumen 928, and six slot-shaped lumens 930.

In FIG. 9C, tubular body 940 includes a plurality of lumens that includes a central lumen 942 and plurality of non-central, surrounding lumens 944. Plurality of surrounding lumens 944 of FIG. 9C includes three circular surrounding lumens 946, one rectangular surrounding lumen 948, and six curvilinear, slot-shaped lumens 950.

Balloon catheter suturing devices and systems provided herein may include a balloon constructed of one or more polymeric, transparent materials. In some cases, at least a portion of the balloon can be constructed of a polymeric fibrous matrix or a polymer film. In various cases, the balloon is constructed of a modified thermoset polymer (also described as a composite of polymeric fibers and polymers).

Figure 10:
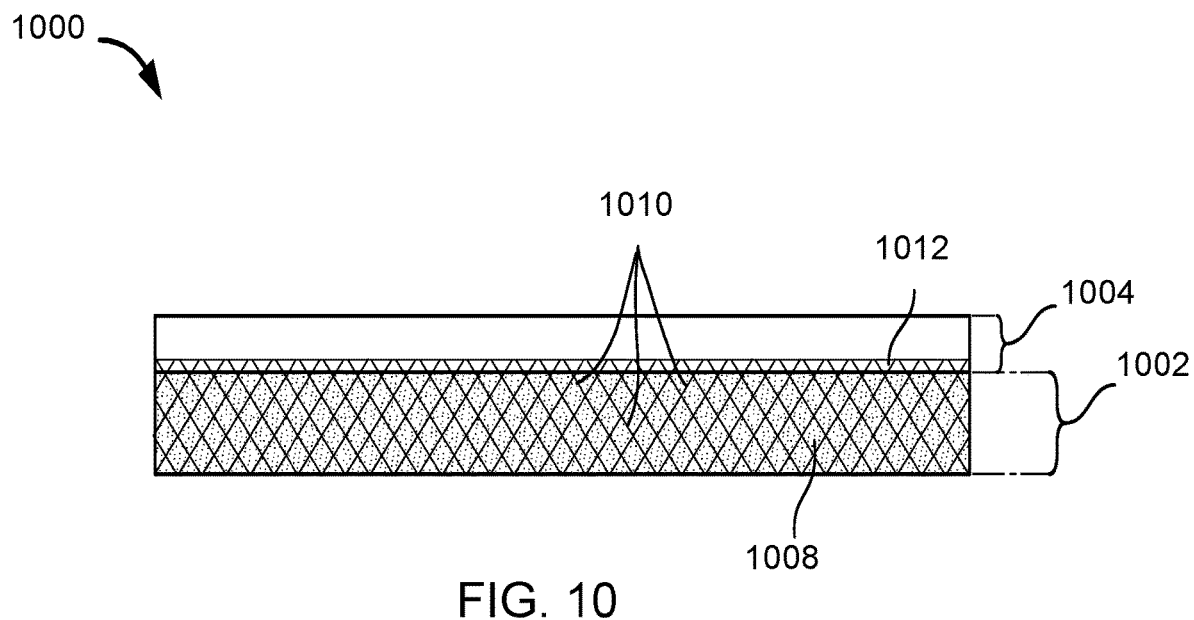
FIG. 10 illustrates a cross-sectional view of a balloon material, which can be used in balloon catheter suturing devices and systems provided herein.
Figure 11B:
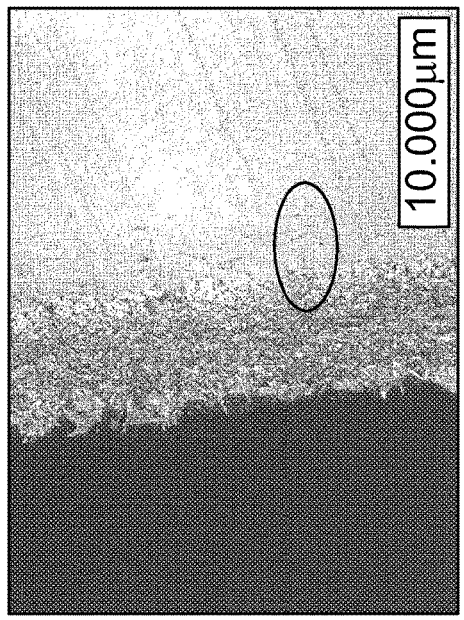
FIGS. 11B-11D are cross-sectional views of composite of silicone and polymeric fibers, which can be used in certain balloon catheter suturing devices and systems provided herein.
Figure 11D:
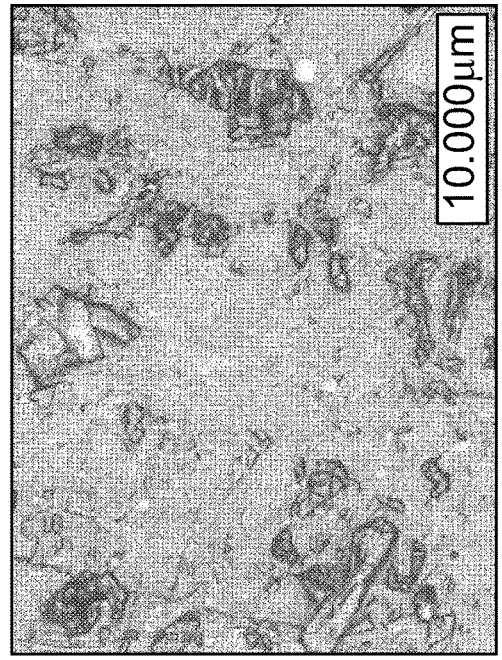
Figure 11A:
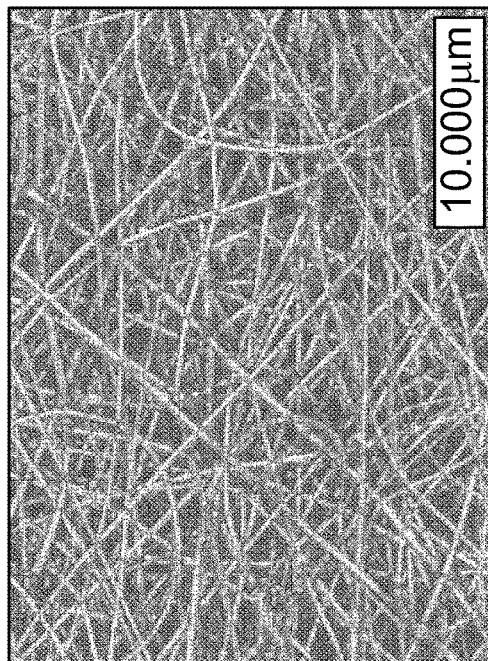
FIG. 11A shows an e-spun fiber network.
Figure 11C:
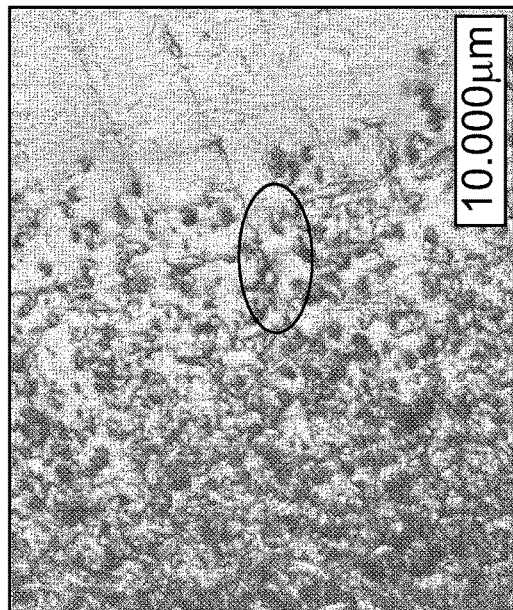

FIG. 10 shows a cross-sectional view of a balloon material that includes a modified thermoset polymer 1000. As shown, polymer 1000 includes an inner layer 1002 (which may also be referred to as a first layer) and an outer layer 1004 (which may also be referred to as a second layer). Inner and outer layers 1002, 1004 of FIG. 10 each includes one or more polymeric materials. In particular, inner layer 1002 of FIG. 10 includes a thermoset polymer 1008 and a plurality of polymeric fibers 1010 (represented by crosshatch lines in the figure) embedded within thermoset polymer 1008. As shown in FIG. 10, thermoset polymer 1008 is embedded with individual fibers that make up the plurality of polymeric fibers 1010. In some cases, polymer 1008 can fully or partially fill space between some of the individual fibers. Described differently, thermoset polymer 1008 can interpenetrate the space between individual fibers that make up the plurality of polymeric fibers 1010. In some cases, thermoset polymer 1008 can covalently bond to the individual fibers. In some cases, polymer 1008 can mechanically engages with the individual fibers by interlocking with at least a portion of the plurality of polymeric fibers 1010. Exemplary materials of various thermoset polymers 1008 include, but are not limited to, polyurethanes, silicones, phenolic polymers, amino polymers, epoxy polymers and combinations thereof. FIGS. 11B-11D depict cross-sectional views of an exemplary composite that includes polymeric fibers embedded within a silicone thermoset polymer.

Suitable silicones may include, but are not limited to, polydimethylsiloxane (PDMS), polydiphenylsiloxane, polymethylphenylsiloxane, fluorosilicones such as poly methyl(3,3,3-trifluoropropyl)siloxane and combinations thereof. The plurality of polymeric fibers 1010 of FIG. 10 can be randomly oriented. In such cases, the plurality of polymeric fibers 1010 may form a nonwoven fibrous matrix. In some cases, the plurality of polymeric fibers 1010 can be oriented in a regular pattern. The plurality of polymeric fibers 1010 oriented in a regular pattern may form a woven fibrous matrix. The nonwoven fibrous matrix can provide the benefit of providing multiaxial strength to a material while the woven fibrous matrix can provide uniaxial strength directed to a particular axis.

Polymeric fibers can be constructed of biocompatible materials including various thermoplastic materials. In particular, fibers may be formed of thermoplastic materials suitable for electrospinning, force spinning or melt-blowing processes. Electrospinning is a process that uses electrical charge to create fibers from a liquid while force spinning is a process that uses centrifugal force to create fibers. Melt-blowing is a process in which a molten thermoplastic resin is extruded through a die and then stretched and cooled with high-velocity air to form long, fine fibers. In some cases, fibers can be constructed of various polymers that exhibit hydrophilic or hydrophobic characteristics. In some cases, fibers can be raw e-spun fibers, such as those shown in FIG. 11A.

Suitable polymers for fibers can be formed from fluoropolymers including, but not limited to, for example, polytetrafluoroethylene (PTFE), polyvinylidene fluoride (PVDF) (e.g. Kynar™ and Solef™), poly(vinylidene fluoride-co-hexafluoropropene) (PVDF-HFP), cyclic fluoropolyethers such as Cytop™, perfluoroalkoxy alkane resins (PFA), poly (pentafluorostyrene), poly(2,2,3,3,4,4,4-heptafluorobutyl methacrylate), fluoroethylene-alkyl vinyl ether (FEVE; Lumiflon™), poly[4,5 difluoro 2,2 bis(trifluoromethyl)-1,3-dioxole-co-tetrafluoroethylene, and combinations thereof. Other suitable polymers for forming fibers are urethane-based polymers that include, but are not limited to, for example, polyurethanes, polyurethane elastomers (e.g. Pellethane), polyether-based polyurethanes (e.g. Tecothane), polycarbonate-based polyurethanes (e.g. Bionate and/or Chronoflex) and combinations thereof. Other examples of suitable polymer materials for fibers can include, but are not limited to, polycarbonate, polyether, polyester, polyamide, nylon 6, nylon 12, nylon 66, nylon 10, nylon 11, polyetherimide and combinations thereof. In some embodiments, fibers are formed from block polymers such as, for example, a poly(styrene-b-isobutylene-b-styrene) (SIBS) tri-block polymer and/or a polyisobutylene polyurethane (PIB-PUR).

Polymeric fibers can have diameters in the range of about 40 nanometers (nm) to 10,000 nm, for example. The fiber diameter size can include a range of about 100 nm to 3,000 nm. In some examples, suitable fiber diameter sizes can include ranges of about 40 nm to 2,000 nm, about 100 nm to 1,500 nm or about 100 nm to 1,000 nm, for example. In still further examples, fibers 412 can have average fiber diameters ranging between about 900 nm to 10,000 nanometers or between about 800 nm to 10,000. In some cases, fibers 912 are nanofibers having diameters less than 1,000 nm. For example, nanofiber diameters can range from about 100 nm to 800 nm, or be any value there between. In some examples, nanofiber diameters can range from 100 nm to 400 nm.

Outer layer 1004 of FIG. 10 can include one or more hydrogels (also described as crosslinkable, hydrophilizing agents). Hydrogels are a network of hydrophilic polymer chains that are bonded together by association bonds, such as hydrogen bonds and intermolecular hydrophobic associations. Hydrogels have structures that are capable of retaining large amounts of water. In various cases, outer layer 1004 includes hydrogels that are optically transparent in vivo, i.e., when placed into a body. In some cases, outer layer 1004 includes hydrogels having anti-fouling properties, for example, are resistant to protein binding and platelet adsorption. In some cases, hydrogels are anti-thrombogenic. Material having anti-fouling properties provide the advantage of being optically transparent for longer durations in vivo. Anti-thromobogenic materials provide implantable components and devices with a benefit of long-term biocompatibility in vivo.

Various suitable hydrogels include, but are not limited to, olefin based polymers such as a polyethylene glycol (PEG) or a PEG derivative, for example, PEG-dimethacrylate, UV-curable PEG, PEG diacrylate, polyethylene glycol-neopentyl glycol diacrylate methyl acrylate (PEG-NPDGA), PEG-Bioslide™, PEG-Z-Glide™, chitosan-PEG, thiol-PEG, maleimide-PEG, amino-PEG, azide-PEG, and carboxyl-PEG. Examples of other suitable hydrogels include, but are not limited to, polyvinylpyrrolidone (PVP), polyvinyl acetate (PVA), glycosaminoglycans (e.g. heparin), poly[N-(2-hydroxypropyl) methacrylamide] (PHPMA), poly(vinyl pyrrolidone), polyethylene/oligoethylene, polyHEMA, polytetraglyme, hyaluronic acid, chitosan and any derivatives thereof.

In some cases, at least a portion of the hydrogel is embedded with a plurality of polymeric fibers 1010. In some cases, the hydrogel can covalently bond to individual fibers that make up the plurality of polymeric fibers 1010. In some cases, the hydrogel can bond to individual fibers by chemical association bonding, such as hydrogen bonding and/or intermolecular hydrophobic associations. In some cases, the hydrogel can mechanically engage with at least a portion of the plurality of polymeric fibers 1010 by interpenetrating space between individual fibers protruding from a surface of an adjacent layer. For example, as shown in FIG. 10, the plurality of polymer fibers 1010 is partially embedded in a portion 1012 of outer layer 1004 located adjacent the inner layer 1002. In some cases, the hydrogel can also be incorporated with a polymer solution from which spun fibers are formed. As a result, hydrophilic polymer chains can be intertwined or entangled with another polymer.

In some cases, selection portions of the different layers shown in FIGS. 10 and/or 11B-11D can be treated to create weakened portions of the balloon to create tear lines for separating a pledget section of a balloon wall. In some cases, the polymeric fiber layers can have be cut along desired tear lines prior to combining the fibers with the thermoset polymer.

Figure 12A:
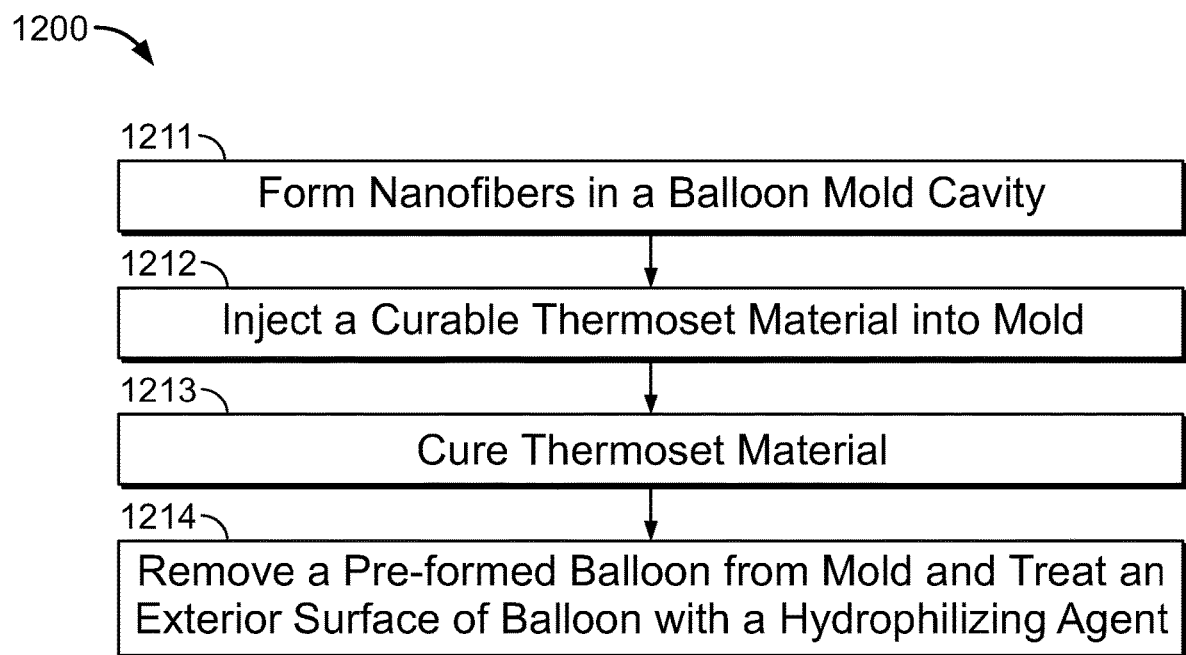
FIGS. 12A-12B and 13 provide flowcharts of methods used for manufacturing balloon catheter suturing devices and systems provided herein.

FIG. 12A is a flowchart of an example method 1200 of manufacturing balloons provided herein, such as balloon 108, 208, 310, 410, 618, 500, 520, 540, 560, 580, and 590, 1810, 1910, or 2010. An initial set of operations 1211, 1212, 1213 forms an inner layer of balloon and any subsequent operations 1214 forms an outer layer of balloon. At operation 1211, a plurality of polymeric nanofibers (or, alternatively, a plurality of polymeric fibers) are formed into an interior cavity of a balloon mold using an electrospinning process. In some cases, the electrospinning process can leave sections uncovered to produce weakened sections. Alternatively, a plurality of polymeric nanofibers can be preformed into a thin, nonwoven fibrous matrix film or sheet. In some cases, a thin, nonwoven fibrous matrix film or sheet can have score lines cut into to produce weakened tear lines. Once preformed, nonwoven fibrous matrix film or sheet can be rolled and placed into the interior cavity of the balloon mold. In some cases, nanofibers may be constructed using processes other than the electrospinning process, for example, a force spinning process.

At operation 1212, a curable thermoset material, e.g. polydimethylsiloxane (PDMS), in liquid form is injected into the mold. Thermoset material at least partially penetrates the plurality of nanofibers.

At operation 1213, thermoset material is cured to form a pre-formed balloon.

At operation 1214, pre-formed balloon is removed from balloon mold and an exterior surface of the pre-formed balloon is treated with a crosslinkable, hydrophilizing agent, such as PEG-dimethacrylate, described herein. Following the treatment, the hydrophilized balloon may continue on to other manufacturing operations to build a direct visualization catheter or an alternative medical device.

Figure 12B:
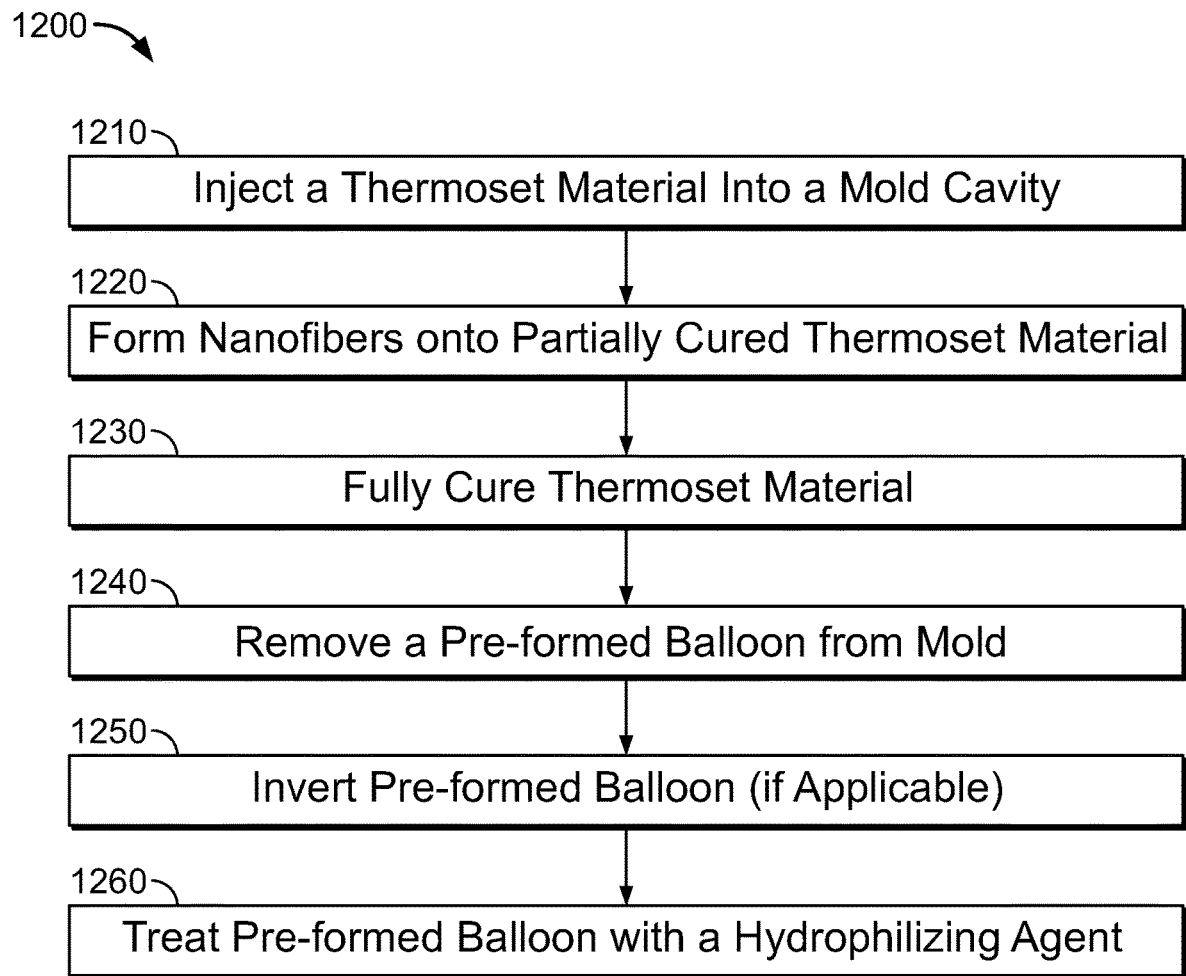

FIG. 12B is a flowchart of another example method 1200 of manufacturing balloons provided herein, such as balloon 108, 208, 308, 408, 500, 520, 540, 560, 580, and 590, or an alternative tubular component. An initial set of operations 1210, 1220, 1230 forms an inner layer of balloon and operation 1260 forms an outer layer of balloon. At operation 1210, thermoset material is injected into a balloon mold using a curable thermoset material and only partially cured.

At operation 1220, a plurality of polymeric nanofibers are formed onto partially cured thermoset material using an electrospinning process or alternative process, such as force spinning. Because thermoset material is not fully cured, at least a portion of plurality of polymeric nanofibers penetrates into thermoset material such that nanofibers are exposed at an exterior surface of balloon. In some cases, the electrospinning process and/or the force spinning process can arrange the delivery of fibers to create weakened tear lines in a resulting balloon.

At operation 1230, thermoset material is cured to form an inner layer of a pre-formed balloon. Thermoset material may be cured as described herein.

At operation 1240, pre-formed balloon is optionally removed from balloon mold and, at operation 1250, performed balloon is inverted such that at least a portion of plurality of polymeric nanofibers are exposed along an exterior surface of balloon. In some cases, operation step 1250 may not be necessary if during operation, at least a portion of the plurality of polymeric nanofibers penetrates into thermoset material such that fibers would be exposed at exterior surface of a non-inverted balloon.

At operation 1260, exterior surface of the pre-formed balloon is treated with a crosslinkable, hydrophilizing agent, e.g., PEG-dimethacrylate, described herein. Following the treatment, a hydrophilized balloon may continue on to other manufacturing operations, if applicable.

Figure 13:
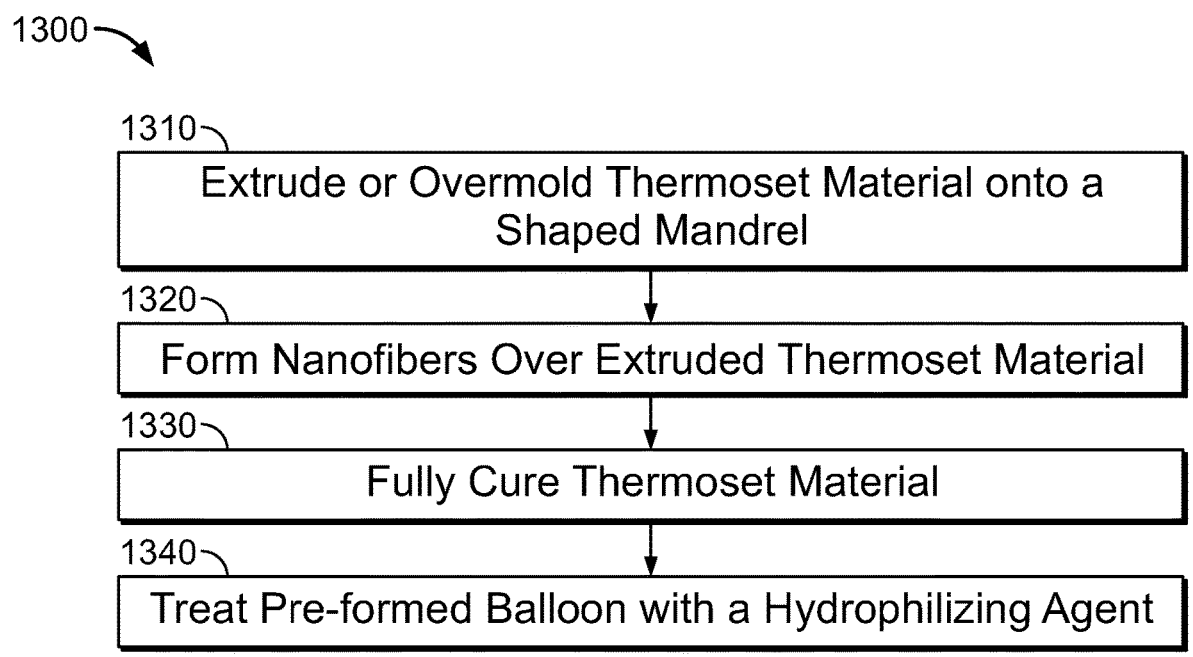

FIG. 13 is a flowchart of another example method 1300 of manufacturing balloons provided herein, such as balloon 108, 208, 308, 408, 500, 520, 540, 560, 580, 590, or an alternative tubular component. An initial set of operations 1310, 1320, 1330 forms an inner layer of balloon and subsequent operation 1340 forms an outer layer of balloon. At operation 1310, a curable thermoset material, e.g. polydimethylsiloxane (PDMS), is extruded or overmolded onto a shaped mandrel. The mandrel can be formed in various balloon shapes or tubular shapes.

At operation 1320, a plurality of polymeric nanofibers are formed on a shaped mandrel using an electrospinning process or a force spinning process. The plurality of polymeric nanofibers are formed onto thermoset material such that at portion of the nanofibers penetrates into thermoset material and another portion of the nanofibers remains exposed at an exterior surface of the balloon. In some cases, the electrospinning process and/or the force spinning process can arrange the delivery of fibers to create weakened tear lines in a resulting balloon.

At operation 1330, thermoset material is fully cured to form an inner layer of a pre-formed balloon. Thermoset material may be cured as described herein.

At operation 1340, the pre-formed balloon is treated with a crosslinkable, hydrophilizing agent, such as PEG-dimethacrylate, described herein. A hydrophilized balloon may be removed from the mandrel at any time after thermoset material has been cured. Hydrophilized balloon may be subject to subsequent manufacturing operations to build a direct visualization catheter or an alternative medical device.

Figure 14:
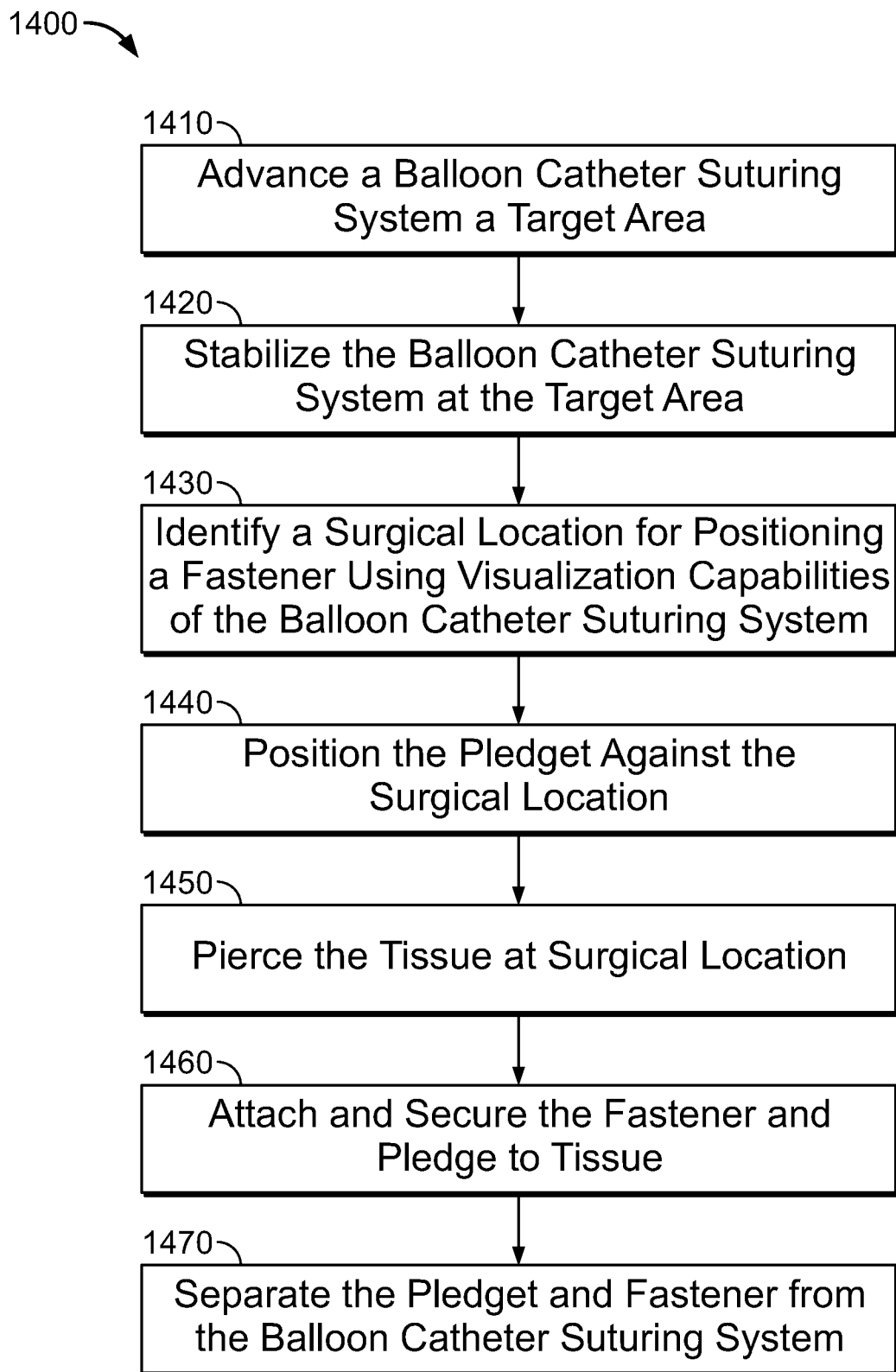
FIG. 14 is a flowchart of a method securing a fastener to tissue during a surgical procedure using balloon catheter suturing devices and system provided herein.

FIG. 14 is a flowchart of a method 1400 for securing a pledget and fastener to a target area, e.g., a left atrium of a heart, during a surgical procedure using a balloon catheter suturing system in accordance with some of the embodiments provided herein. At operation 1410, a target area within a patient can be located and initially inspected by advancing at least a portion of the balloon catheter suturing system to the target area. In some cases, balloon catheter suturing system or portions thereof, e.g., a visualization portion, is advanced to the target area to provide visual or ultrasound images of the target area. In some cases, the balloon catheter suturing system or portions thereof, e.g., a visualization portion, can be advanced to the target area over a guidewire or within a guide catheter. Once at the target area, the balloon catheter suturing system or portions thereof can provide direct visual images or ultrasound images for the inspection. In some cases, inspection can also include injecting contrast media into the targeted area and viewing the area using fluoroscopic equipment.

At operation 1420, the balloon catheter suturing system, is advanced to the target area and a portion thereof expanded at the target area to stabilize the balloon catheter suturing system. In some cases, a balloon or stent is expanded to stabilize the balloon catheter suturing system.

At operation 1430, a desired surgical location at the target area can be verified by using direct visual or ultrasound imaging provided by the balloon catheter suturing system. In some cases, a primary camera located in balloon or stent portion of catheter can be used to verify the surgical location. In some cases, the balloon catheter suturing system includes a secondary visualization portion that can be used in conjunction with the primary camera to visually verify the surgical location. In such cases, primary camera may provide anterior visual images and the secondary visualization portion may provide posterior visual images. At operation 1440, the balloon catheter suturing system can be manipulated such that a pledget or pledget section of a balloon is positioned near or at the desired surgical location. In some cases, a distal end portion of direct visualization catheter can be deflected at a specific angle to position one or more pledgets in a desired location. In some cases, a select portion of direct visual catheter is advanced to the desired location.

At operation 1450, the tissue is pierced using a fastening tool. In some cases, a portion of the balloon catheter suturing system, e.g., a needle, can be used to pierce tissue at the surgical location. In some cases, the balloon catheter suturing system can advance a fastener, such as a staple or clasp, such that the fastener pierces the tissue at the surgical location and a pledget section of a balloon. In some cases, the advancement of the fastener can interlock the fastener with a pledget.

At operation 1460, fastener is attached to tissue and the pledget or pledget section of a balloon. In some cases, attaching the fastener to tissue can include securing a suture through tissue at the surgical location and through a hole in a pledget. In some cases, attaching fastener to tissue can include attaching a pledget, staple or clasp to tissue at the surgical location through a pledget section of a balloon wall.

At operation 1470, the fastener and pledget are released from the balloon catheter suturing system. In some cases, a pledget section of a balloon wall is torn away from the balloon by retracting the balloon. In some cases, the pledget is released from the catheter using an actuator at a proximal end of the balloon catheter suturing system. In some cases, fastener is released from the catheter using an actuator at a proximal end of the balloon catheter suturing system. In some cases, pledget and/or fastener is released from the catheter by advancing a portion of the catheter, e.g., a pusher rod, to push the fastener away from a distal end of the catheter. In some cases, pledgets and/or fastener, such as a suture thread, may not be released from the catheter until multiple surgical areas have been secured with the fasteners and pledgets.

Figure 15:
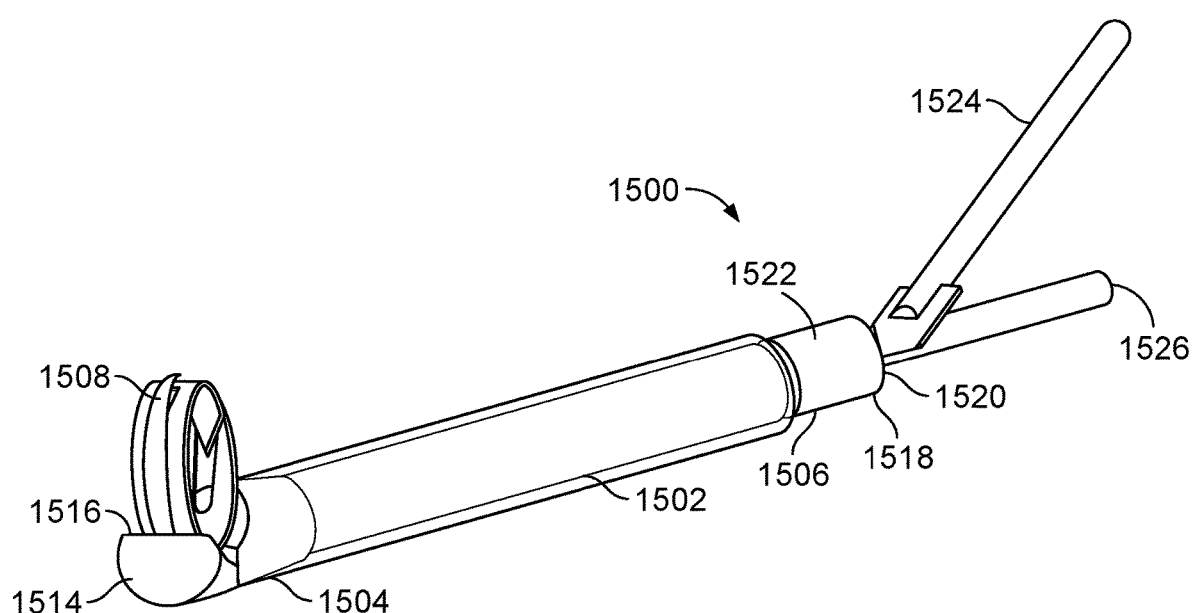
FIG. 15 shows an exemplary fastening portion, which can be used with or in balloon catheter suturing devices and systems provided herein.

FIG. 15 shows an exemplary fastening tool 1500, which can be used in balloon catheter suturing systems provided herein. Fastening tool 1500 includes a tubular main body 1502 with a distal end portion 1504, a proximal end portion 1506, and a lumen (not shown) therethrough that is sized to receive a fastener 1508. As shown, tubular main body 1502 can be generally straight. In some cases, a portion of tubular main body 1502, e.g., a distal end portion 1504, can be pre-formed to bend at a suitable angle or have a curvature that allows fastening tool 1500 to better access target tissue areas during a surgical procedure. In some cases, tubular main body 1502 can be deflectable such that the distal end portion 1504 can deflect to different angles during the procedure.

Distal end portion 1504 of fastening tool 1500 includes a distal end 1514 and defines a distal opening 1516 adapted to receive and temporarily retain fastener 1508. As shown in FIG. 15, in some cases, opening 1516 is adapted to retain a ring-shaped fastener 1508. Fastening tool 1500 can be coupleable to various types of fasteners 1508, for example, suture, a suture with a pledget, clips, and/or staples. Fastening tool 1500 can be used to deliver and affix fastener 1508 to tissue, e.g., annulus of a heart valve.

Proximal end portion 1506 can include a proximal end 1518 and defines a proximal opening 1520 adapted to receive fastener 1508. In FIG. 15, proximal end portion 1506 has a sleeve 1522 adapted to receive at least one rod, e.g., a push rod 1524 and/or an insertion rod 1526. Insertion rod 1526 can be used to load fastener 1508 into sleeve 1522. Push rod 1524 can be used to advance fastener 1508 through sleeve 1522 into tubular main body 1502. Push rod 1524 can be sized and shaped to be received through a lumen (not shown) of tubular main body 1502 and be extended from distal opening 1516. In some cases, a single rod can be used as both push rod 1524 and insertion rod 1526.

Figure 16A:
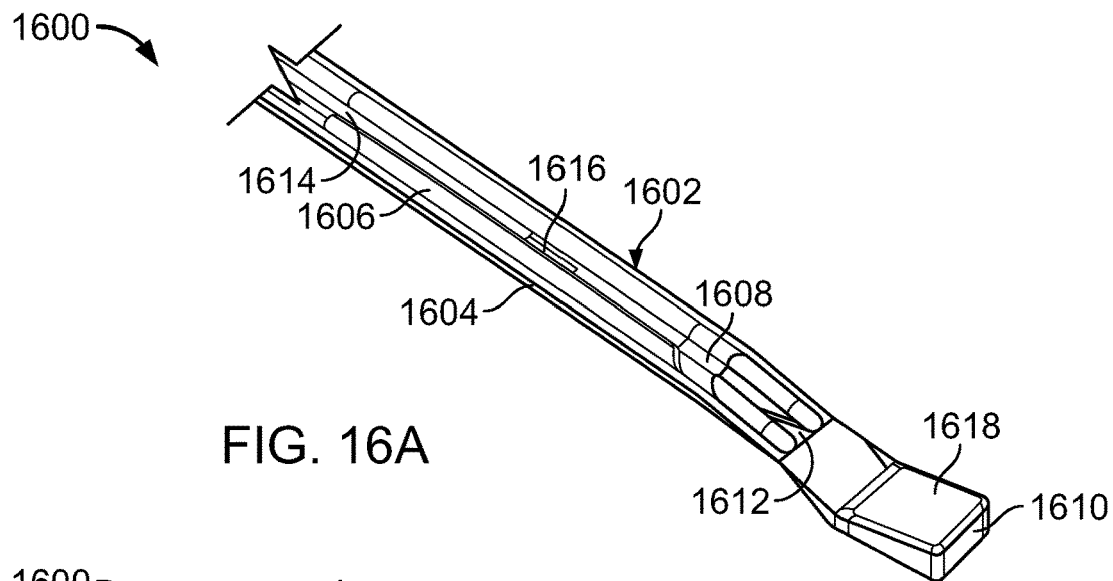
FIGS. 16A-16C show cross-sectional views of an exemplary fastening portion at a distal end portion.
Figure 16B:
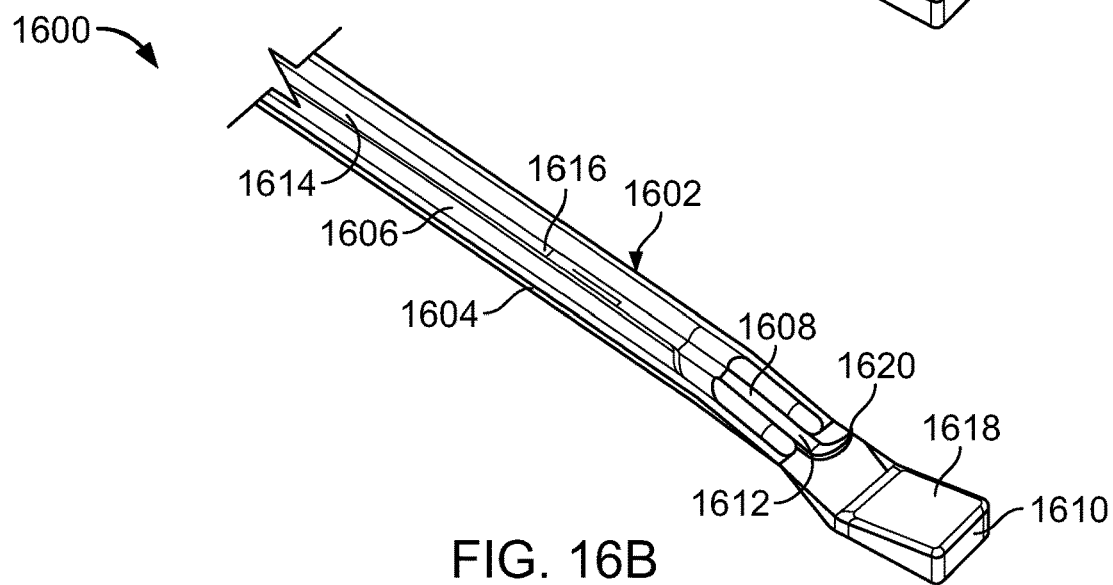
Figure 16C:
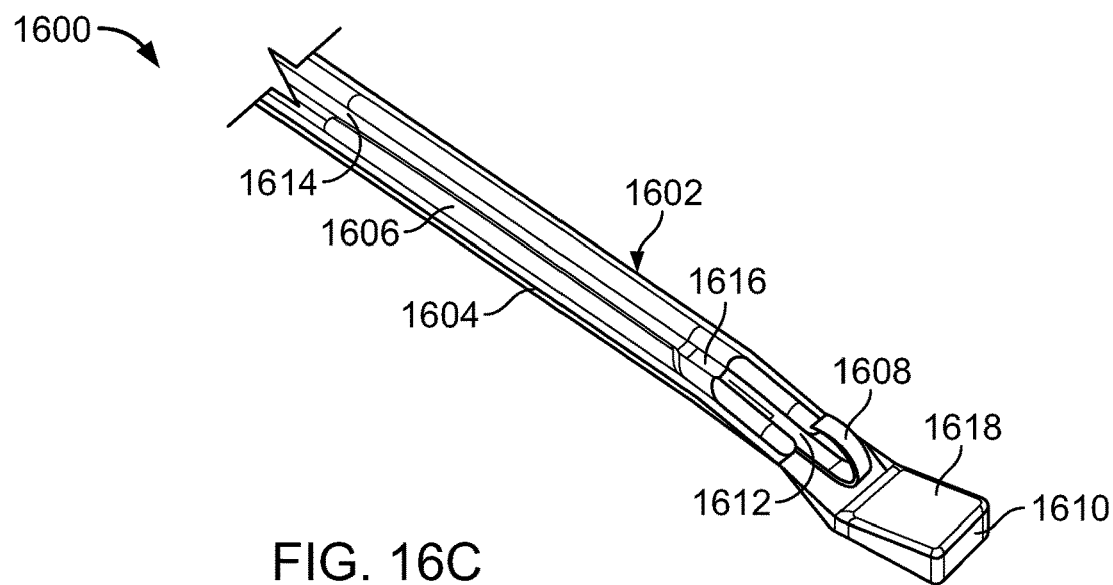

FIGS. 16A-16C show cross-sectional views of an exemplary fastening tool 1600, which can be used in balloon catheter suturing systems provided herein, at a distal end portion 1602. Fastening tool 1600 can include a tubular body 1604 defining a lumen 1606 adapted to receive a fastener 1608, e.g., an annulus clasp, and a distal end 1610 defining a distal opening 1612. As shown in FIGS. 16A-16C, fastener 1608 can be advanced through distal end portion 1602 of fastening tool 1600 and released from fastening tool 1600 at distal opening 1612. Lumen 1606 can be sized and shaped to receive fastener 1608. Lumen can also be sized and shaped to receive at least a portion of a push rod 1614. Push rod 1614 can be used to about a proximal end 1616 of fastener 1608 and be translated distally to push fastener 1608 to distal end 1610 of fastening tool 1600. Distal opening 1612 can be adapted to allow fastener 1608 to pass through. As shown, in some cases, distal end 1610 can include a sensor 1618 that indicates when fastener 1608 has reached distal opening 1612. Sensor 1618 can provide location information of fastener 1608 to indicate when fastener 1608 is ready to be released from fastening tool 1600. Sensor 1618 may also be used to prevent accidental release of fastener 808.

In FIG. 16A, push rod 1614 and fastener 1608 are located at distal end portion 1602 of fastening tool 1600 proximate to distal opening 1612. In FIG. 16B, push rod 1614 and fastener 1608 are distally translated such that distal end 1620 of fastener 1608 begins to emerge from distal opening 1612. In some cases, as shown, distal end 1620 of fastener 1608 can begin to form into a preformed shape, e.g., begin to curl into a ring-like clasp. In FIG. 16C, push rod 1614 is further distally translated such that fastener 1608 extends from distal opening 1612 in a partially deployed state. As shown in FIG. 16C, fastener 1608 can curl into a semi-circular shape in partially deployed state. Fastener 1608 can be fully deployed to form a full ring by further distally translating push rod 1614 such that fastener extends completely from distal opening 1612. Fastener 1608 can be transitioned from the partially deployed state to the fully deployed after the device has been properly positioned at a target surgical location. Fastener 1608 can be fastened to tissue when transitioned from the partially deployed state to the fully deployed state. In some cases, sensor 1618 can be used to identify that fastener 1608 is ready to be fully deployed prior to being released from fastening tool 1600.

Figure 17A:
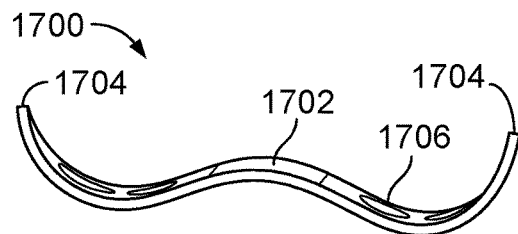
FIGS. 17A-17G show various exemplary fasteners.
Figure 17B:
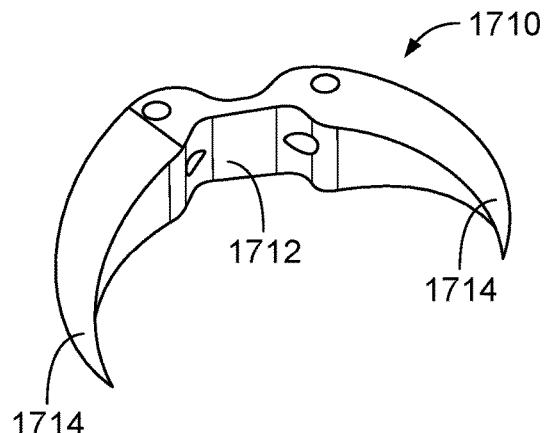
Figure 17C:
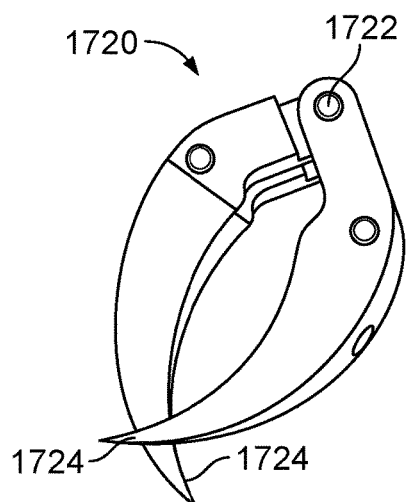
Figure 17D:
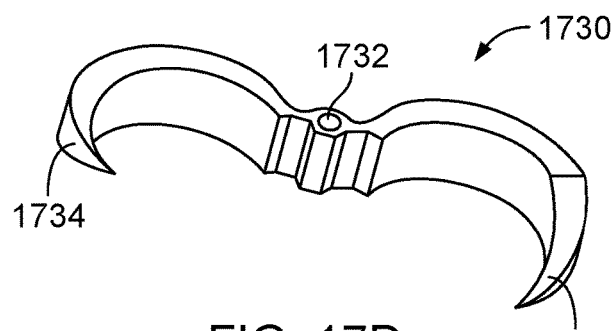

FIGS. 17A-17G show various exemplary fasteners 1700, 1710, 1720, 1730, 1740. As discussed herein, fasteners can be formed of various shapes and sizes. Suitable types of fasteners include, but are not limited to, for example, a suture, staple, hook, tack, clamp or a clip. Fasteners can be made of various polymeric and metallic materials. Suitable materials for fasteners include, but are not limited to, for example, polyethylene, polypropylene, polycarbonate, PEEK, stainless steel, nitinol and combinations thereof. As shown in FIGS. 17A and 17B, fastener 1700, 1710 can be a single body 1702, 1712 with sharp tips 1704, 1714 adapted to penetrate tissue on each end. As shown in FIG. 17A, body 1702 of fastener 1700 can define at least one thru-hole 1706. In some cases, thru-hole can be sized to receive a suture (not shown). A single body fastener 1700, 1710 can be reshaped such that sharp tips 1704, 1714 can be easily joined together and attached to tissue. As shown in FIGS. 17C and 17D, fastener 1720, 1730 can include two or more portions coupled together by a hinge connector 1722, 1732 that allows tissue penetrating tips 1724, 1734 to join together. Possible fastener designs are not limited by the examples provided herein, as one skilled in the art could contemplate other various structures that could be used to penetrate tissue and/or connect suture to tissue.

Figures 17E, 17F:
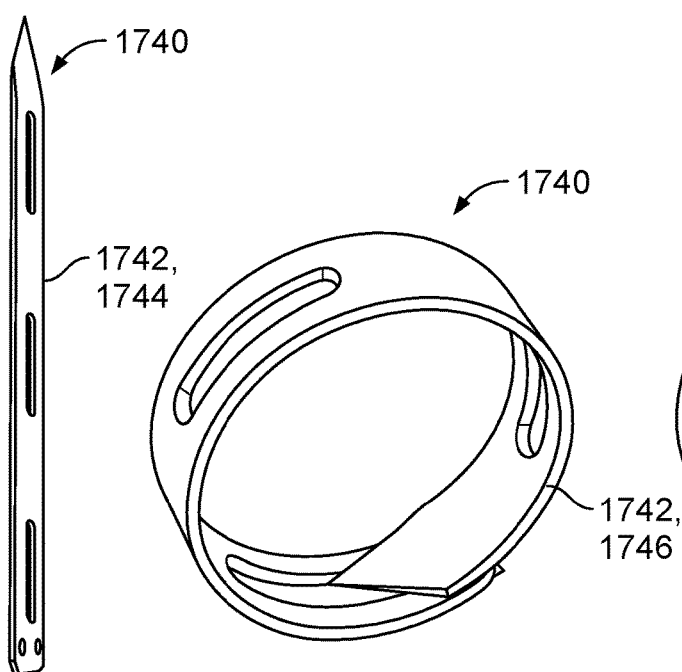
Figure 17G:
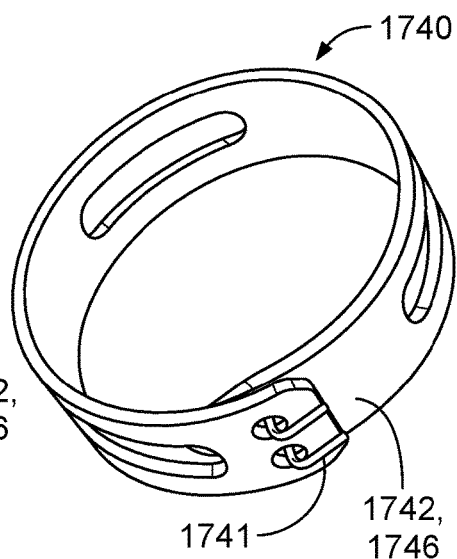

FIGS. 17E-17G show another exemplary fastener 1740 that can be formed of a single body 1742 that can be shaped into multiple configurations. Fastener 1740 can be shaped in a first configuration (see FIG. 17E) prior to implantation and a second configuration (see FIGS. 17F and 17G) during and after implantation. In some cases, fastener 1740 can be made of a shape memory material or a malleable material. Fastener 1740 can be made of various shape memory metals or polymers and be pre-formed into a desired final shape. In some cases, fastener 1740 can be fixed into second configuration by a connector, such as a clip 1741, as shown in FIG. 17G.

As shown in FIG. 17E, fastener can be shaped as a flat segment 1744 in first configuration when being delivered by a direct visualization catheter (or a direct visualization system) to a surgical site. Fastener can form into the desired final shape, e.g., a ring-like clasp 1746 as shown in FIGS. 17F and 17G, in second configuration when implanted into a patient.

A number of embodiments of the direct visualization devices, systems, and methods have been described. Nevertheless, it will be understood that various modifications may be made without departing from the spirit and scope of the subject matter described herein. Accordingly, other embodiments are within the scope of the following claims.

What is claimed is:

1. A balloon catheter suturing system comprising:
   an elongate shaft defining a lumen and having a distal end portion and a proximal end portion;
   a balloon attached to the distal end portion, the balloon being a weeping balloon having a transparent wall defining at least one detachable section; and
   a suturing tool positionable within the elongate shaft to pass one or more fasteners therethrough, wherein the suturing tool is configured to pass the one or more fasteners through the at least one detachable section.

2. The balloon catheter suturing system of claim 1, wherein the weeping balloon includes at least three punctured holes through a wall thereof.

3. The balloon catheter suturing system of claim 2, wherein the weeping balloon allows for an inflation media flow rate of between 1 and 50 ml per minute.

4. The balloon catheter suturing system of claim 1, wherein the weeping balloon has a plurality of pores, with a greater pore density in a center of a field of view through the elongate shaft and a lower pore density around a periphery of the field of view.

5. The balloon catheter suturing system of claim 1, wherein the transparent wall comprises at least a first layer comprising a thermoset polymer and a plurality of polymeric fibers at least partially embedded in the thermoset polymer.

6. The balloon catheter suturing system of claim 5, wherein the transparent wall comprises at least a second layer disposed on the first layer.

7. The balloon catheter suturing system of claim 6, wherein the second layer comprises a hydrogel.

8. The balloon catheter suturing system of claim 7, wherein the hydrogel comprises polyethylene glycol (PEG).

9. The balloon catheter suturing system of claim 7, wherein the hydrogel envelopes about a portion of the plurality of polymeric fibers protruding from the first layer and mechanically engages with a portion of plurality of polymeric fibers.

10. The balloon catheter suturing system of claim 9, wherein the thermoset polymer comprises polydimethylsiloxane (PDMS).

11. The balloon catheter suturing system of claim 5, wherein the plurality of polymeric fibers are electrospun fibers.

12. The balloon catheter suturing system of claim 5, wherein the plurality of polymeric fibers are randomly oriented within the thermoset polymer.

13. The balloon catheter suturing system of claim 5, wherein the plurality of polymeric fibers comprises a polyurethane.

14. The balloon catheter suturing system of claim 5, wherein the thermoset polymer comprises a silicone.

15. The balloon catheter suturing system of claim 1, wherein the transparent wall comprises weakened sections defining one or more tear lines around the at least one detachable section.

16. The balloon catheter suturing system of claim 15, wherein the transparent wall is resistant to tearing along lines other than the one or more tear lines around the at least one detachable section.

17. The balloon catheter suturing system of claim 1, wherein the transparent wall defines at least two detachable sections.

18. A balloon catheter suturing system comprising:
- an elongate shaft defining a lumen and having a distal end portion and a proximal end portion;
- a weeping balloon attached to the distal end portion, the weeping balloon having a transparent wall defining a plurality of pores extending therethrough and at least two detachable sections; and
- a suturing tool positionable within the elongate shaft to pass one or more fasteners through the at least two detachable sections.

19. The balloon catheter suturing system of claim 18, wherein the transparent wall comprises at least a first layer comprising a thermoset polymer and a plurality of polymeric fibers at least partially embedded in the thermoset polymer.

* * * * *